(12) United States Patent
Horn et al.

(10) Patent No.: US 9,956,269 B2
(45) Date of Patent: *May 1, 2018

(54) METHOD FOR IMPROVING THE STABILITY OF PURIFIED FACTOR VIII AFTER RECONSTITUTION

(71) Applicant: CSL Limited, Victoria (AU)

(72) Inventors: Carsten Horn, Marburg (DE); Sabine Zollner, Muri (CH); Hubert Metzner, Marburg (DE); Stefan Schulte, Marburg (DE)

(73) Assignee: CSL Limited, Victoria (AU)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/156,744

(22) Filed: May 17, 2016

(65) Prior Publication Data
US 2016/0367641 A1    Dec. 22, 2016

Related U.S. Application Data

(63) Continuation of application No. 14/351,513, filed as application No. PCT/EP2012/070701 on Oct. 18, 2012, now Pat. No. 9,394,353.

(60) Provisional application No. 61/548,601, filed on Oct. 18, 2011.

(30) Foreign Application Priority Data

Oct. 18, 2011 (EP) ..................................... 11185651

(51) Int. Cl.
A61K 38/00 (2006.01)
C07K 16/00 (2006.01)
A61K 38/37 (2006.01)
C07K 14/755 (2006.01)

(52) U.S. Cl.
CPC ............ *A61K 38/37* (2013.01); *C07K 14/755* (2013.01)

(58) Field of Classification Search
None
See application file for complete search history.

(56) References Cited

U.S. PATENT DOCUMENTS

| | | | |
|---|---|---|---|
| 4,757,006 A | 6/1988 | Toole, Jr. et al. |
| 4,868,112 A | 9/1989 | Toole, Jr. |
| 5,171,844 A | 12/1992 | Van Ooyen et al. |
| 5,422,260 A | 6/1995 | Kaufman et al. |
| 5,565,427 A | 10/1996 | Freudenberg |
| 5,605,884 A | 2/1997 | Lee et al. |
| 5,661,008 A | 8/1997 | Almstedt et al. |
| 6,228,613 B1 | 5/2001 | Fischer et al. |
| 6,599,724 B1 | 7/2003 | Mikaelsson et al. |
| 7,041,635 B2 | 5/2006 | Kim et al. |
| 2002/0132306 A1 | 9/2002 | Kaufman et al. |

FOREIGN PATENT DOCUMENTS

| | | |
|---|---|---|
| EP | 0 265 778 | 5/1988 |
| EP | 0 294 910 | 12/1988 |
| EP | 0 295 597 | 12/1988 |
| EP | 0 303 540 | 2/1989 |
| WO | WO 88/00831 | 2/1988 |
| WO | WO 88/05825 | 8/1988 |
| WO | WO 97/40145 | 10/1997 |
| WO | WO 00/24759 | 5/2000 |
| WO | WO 01/70968 A2 | 9/2001 |
| WO | WO 02/102850 A2 | 12/2002 |
| WO | WO 2004/067566 A1 | 8/2004 |
| WO | WO 2004/101740 A2 | 11/2004 |
| WO | WO 2008/005847 A2 | 1/2008 |
| WO | WO 2008/077616 A1 | 7/2008 |
| WO | WO 2010/111414 A1 | 9/2010 |
| WO | WO 2011/020866 A2 | 2/2011 |
| WO | WO 2011/027152 A1 | 3/2011 |

OTHER PUBLICATIONS

Advate© FDA package insert, revised Apr. 2014, initial U.S. approval: 2003.
Amano et al., "Mutation at either Arg336 or Arg562 in Factor VIII is Insufficient for Complete Resistance to Activated Protein C (APC)-mediated Inactivation: Implications for the APC Resistance Test", Thromb. Haemost, vol. 79, pp. 557-563 (1998).
Ananyeva et al., "Catabolism of the Coagulation Factor VIII", TCM, vol. 11, No. 6, pp. 251-257 (2001).
Bi et al., "Further characterization of factor VIII-deficient mice created by gene targeting: RNA and protein studies", Blood, vol. 88, pp. 3446-3450 (1996).
Bi et al., "Targeted disruption of the mouse factor VIII gene produces a model of haemophilia A", Nature genetics, vol. 10, pp. 119-121 (1995).
Björkman, S., "Prophylactic Dosing of Factor VIII and Factor IX from a Clinical Pharmacokinetic Perspective", Haemophilia vol. 9, Suppl. 1, (2002) pp. 101-110.
Di Paola et al., "ReFacto® and Advate®: a single-dose, randomized, two-period crossover pharmacokinetics study in subjects with haemophilia A", Haemophilia, vol. 13, pp. 124-130 (2007).
Donath et al., "Characterization of des-(741-1668)-factor VIII, a single-chain factor VIII variant with a fusion site susceptible to proteolysis by thrombin and factor Xa", Biochem. J., Vo. 312, pp. 49-55 (1995).

(Continued)

*Primary Examiner* — Jeanette Lieb
(74) *Attorney, Agent, or Firm* — Finnegan, Henderson, Farabow, Garrett & Dunner, LLP

(57) ABSTRACT

The present disclosure relates to a method for increasing the stability of a Factor VIII molecule after purification, lyophilization and reconstitution, comprising preventing proteolytic cleavage of the Factor VIII molecule into a first fragment comprising essentially the A1 domain and the A2 domain and a second fragment comprising essentially the A3 domain, the C1 domain and the C2 domain throughout manufacturing the Factor VIII molecule. The disclosure further pertains to a method for improving the bioavailability of Factor VIII after intravenous and non-intravenous injection.

18 Claims, 9 Drawing Sheets

(56) References Cited

OTHER PUBLICATIONS

Eaton et al., "Construction and Characterization of an Active Factor VIII Variant Lacking the Central One-Third of the Molecule", Biochemistry, vol. 25, No. 26, pp. 8343-8347 (1986).
Esmon et al., "Characterization of recombinant factor VIII and a recombinant factor VIII deletion mutant using a rabbit immunogenicity model system", Blood, vol. 76, pp. 1593-1600 (1990).
Extended European search report from the European Patent Office in corresponding EP 11 18 5651 from Munich, dated Feb. 1, 2012.
Foster et al., "Factor VIII Structure and Function," *Blood Reviews*, 3:180-191 (1989).
Gale et al., "Intrinsic stability and functional properties of disulfide bond-stabilized coagulation factor VIIIa variants" Journal of Thrombosis and Haemostasis, vol. 4, pp. 1315-1322 (2006).
Herlitschka et al., "High expression of a B-domain deleted factor VIII gene in a human hepatic cell line", Journal of Biotechnology, vol. 61, pp. 165-173 (1998).
HFA, Hemophilia, http://www.hemophiliafed.org/bleeding-disorders/hemophilia/causes/, last visited May 1, 2015.
International Preliminary Report on Patentability for Application No. PCT/EP2012/070701, dated Apr. 22, 2014, 7 pages.
International Search Report from the European Patent Office for International Application No. PCT/EP2012/070701 dated Jan. 2, 2013.
Kaufman, R., "Expression and Structure-Function Properties of Recombinant Factor VIII", Transfusion Medicine Reviews, vol. VI, No. 4, pp. 235-246 (1992).
Kelly et al., "An improved manufacturing process for Xyntha/ReFacto AF," *Haemophilia*, (2010) 16(5):7171-25.
Krishnan et al., "Thrombin cleavage analysis of a novel antihaemophilic factor variant, factor VIII Delta II", Eur. J. Biochem, vol. 195, pp. 637-644 (1991).
Lenting et al., "The Life Cycle of Coagulation Factor VIII in View of Its Structure and Function", Blood, vol. 92, pp. 3983-3996 (1998).
Lollar, P., "Characterization of Factor VIII B-Cell Inhibitory Epitopes", Thrombosis and Haemostasis, vol. 82, pp. 505-508 (1999).
Miao et al., "Bioengineering of coagulation factor VIII for improved secretion", Blood, vol. 103, No. 9, pp. 3412-3419 (2004).
Novoeight® FDA package insert, revised Sep. 2015, initial U.S. approval: 2013.
Nuwiq® FDA package insert, revised Sep. 2015, initial U.S. approval: 2015.
Oh et al., "Synthesis of recombinant blood coagulation factor VIII (FVIII) heavy and light chains and reconstitution of active form of FVIII, "Experimental and Molecular Medicine, vol. 31, No. 2, pp. 95-100 (1999).
Pabinger I., "Pharmacokinetic results from a Phase I/III study of a novel recombinant single-chain Factor VIII (rVIII-SingleChain) compared to octocog alfa in severe haemophilia A patients," *International CSL627_1001 study group*, (undated).
Pabinger I., "Pharmacokinetic results from a Phase I/III study of a novel recombinant single-chain Factor VIII (rVIII-SingleChain) compared to octocog alfa in severe haemophilia A patients," *International Society on Thrombosis and Haemostasis*, 11:Suppl. 2, 290-1019 (abstract) (2013).
Patent Examination Report No. 1 issued from the Australian Government, IP Australia, on Aug. 1, 2014, in corresponding Australian patent application No. 2012318292.
Pipe, S., "Coagulation Factors with Improved Properties for Hemophilia Gene Therapy", Seminars in Thrombosis and Hemostasis, vol. 30, No. 2, pp. 227-237 (2004).
ReFacto® FDA annotated package insert, initial U.S. approval: 2000.
Rizza et al., "Coagulation Assay of VIIIC and IXC", in Bloom ed. The Hemophilias, Churchill Livingston, NY, pp. 18-38 (1992).
Robinson et al., "Optimizing the stability of single-chain proteins by linker length and composition mutagenesis", Proc. Natl. Acad. Sci. USA, vol. 95, pp. 5929-5934 (1998).
Rosen, S., "Assay of Factor VIII:C with a Chromogenic Substrate", Scand J. Haematol, vol. 33, pp. 139-145 (1984).
Sandberg et al., "Structural and Functional Characterization of B-Domain Deleted Recombinant Factor VIII", Seminars in Hematology, vol. 38, No. 2, Suppl. 4, pp. 4-12 (2001).
Shapiro, A.D., "Why is Primary Prophylaxis Underutilized in the United States?", Haemophilia, vol. 9 (2003), pp. 670-672.
Swaroop et al., "Mutagenesis of a Potential Immunoglobulin-binding Protein-binding Site Enhances Secretion of Coagulation Factor VIII", the Journal of Biological Chemistry, Vo. 272, No. 39, pp. 24121-24124 (1997).
Takedani, H., "Continuous infusion during total joint arthroplasty in Japanese haemophilia A patients: comparison study among two recombinants and one plasma-derived factor VIII", Haemophilia, vol. 16, pp. 740-746 (2010).
The Diagnosis, Evaluation, and Management of von Willebrand Factor Disease, NIH Publication No. 08-5832 Dec. 2007.
Toole et al., "A large region (=95 kDa) of human factor VIII is dispensable for in vitro procoagulant activity", Proc. Natl. Acad. Sci. USA, vol. 83, pp. 5939-5942 (1986).
Wakabayashi et al., "A Glu113Ala Mutation within a Factor VIII $Ca^{2+}$-Binding Site Enhances Cofactor Interactions in Factor Xase", Biochemistry, vol. 44, pp. 10298-10304 (2005).
Written Opinion of the International Search Authority from the European Patent Office for International Application No. PCT/EP2012/070701 dated Jan. 2, 2013.
Xyntha® FDA package insert, revised Oct. 2014, initial U.S. approval: 2008.
Zollner et al., "Non-clinical pharmacokinetics and pharmacodynamics of rVIII-SingleChain, a novel recombinant single-chain factor VIII," *Thrombosis Research*, 134(1):125-131 (2014).
Zollner et al., "Preclinical efficacy and safety of rVIII-SingleChain (CSL627), a novel recombinant single-chain factor VIII," *Thrombosis Research*, 132:280-287 (2013).
Lee, "The use of recombinant Factor VII products in previously treated patients with hemophilia A: pharmacokinetics, efficacy, safety, and inhibitor development," *Seminars in Thrombosis and Hemostasis*, 2002; 28(3): 241-246.

Stability of FVIII molecules in plasma (ex-vivo)

Stability of FVIII molecules in plasma (in-vivo) of cynomolgus monkeys (dosed at 250 IU/kg)

Thrombin generation in hemophilia A mice (ex vivo)

Stability of FVIII molecules in plasma (in-vivo) of vWF deficient mice

FIG. 9

Domain structure of mature human factor VIII

| A1 | a1 | A2 | a2 | B | a3 | A3 | C1 | C2 |

METHOD FOR IMPROVING THE STABILITY OF PURIFIED FACTOR VIII AFTER RECONSTITUTION

This is a continuation of application Ser. No. 14/351,513, now U.S. Pat. No. 9,394,353, issued Jul. 19, 2016, having a 35 U.S.C. § 371(c) date of Apr. 11, 2014, which is the national stage entry of International Application No. PCT/EP2012/070701, filed Oct. 18, 2012, which claims priority to U.S. Provisional Application No. 61/548,601, filed Oct. 18, 2011, and also claims priority to European Patent Application No. 11185651.4, filed Oct. 18, 2011, all of which are incorporated herein by reference.

The present invention relates to a method for increasing the stability of a Factor VIII molecule after purification, lyophilization and reconstitution, comprising preventing proteolytic cleavage of the Factor VIII molecule into a first fragment comprising essentially the A1 domain and the A2 domain and a second fragment comprising essentially the A3 domain, the C1 domain and the C2 domain throughout manufacturing of the Factor VIII molecule. The invention further pertains to a method for improving the bioavailability of Factor VIII after intravenous and non-intravenous injection.

BACKGROUND OF THE INVENTION

Classic hemophilia or hemophilia A is an inherited bleeding disorder. It results from a chromosome X-linked deficiency of blood coagulation Factor VIII, and affects almost exclusively males with an incidence of between one and two individuals per 10,000. The X-chromosome defect is transmitted by female carriers who are not themselves hemophiliacs. The clinical manifestation of hemophilia A is an increased bleeding tendency. Before treatment with Factor VIII concentrates was introduced the mean life span for a person with severe hemophilia was less than 20 years. The use of concentrates of Factor VIII from plasma has considerably improved the situation for the hemophilia patients increasing the mean life span extensively, giving most of them the possibility to live a more or less normal life. However, there have been certain problems with the plasma derived concentrates and their use, the most serious of which have been the transmission of viruses. So far, viruses causing AIDS, hepatitis B, and non-A non-B hepatitis have hit the population seriously. Since then different virus inactivation methods and new highly purified Factor VIII concentrates have recently been developed which established a very high safety standard also for plasma derived Factor VIII.

Several recombinant and plasma-derived, therapeutic polypeptides, e.g. blood coagulation factors, are commercially available for therapeutic and prophylactic use in humans. FVIII is a blood plasma glycoprotein of up to about 280 kDa molecular mass, produced in the liver of mammals. It is a critical component of the cascade of coagulation reactions that lead to blood clotting. Within this cascade is a step in which factor IXa (FIXa), in conjunction with activated factor VIM (FVIIIa), converts factor X (FX) to an activated form, FXa. FVIIIa acts as a cofactor at this step, being required together with calcium ions and phospholipids for maximizing the activity of FIXa.

An important advance in the treatment of hemophilia A has been the isolation of cDNA clones encoding the complete 2,351 amino acid sequence of human FVIII (U.S. Pat. No. 4,757,006) and the provision of the human FVIII gene DNA sequence and recombinant methods for its production).

Factor VIII is synthesized as a single polypeptide chain with a molecular weight of about 280 kDa. The amino-terminal signal peptide is removed upon translocation of factor VIII into the endoplasmatic reticulum, and the mature (i.e. after the cleavage of the signal peptide) native Factor VIII molecule is then proteolytically cleaved after amino acid residues 1313 and 1648 in the course of its secretion. This results in the release of a heterodimer which consists of a C-terminal light chain of about 80 kDa in a metal ion-dependent association with an about 160-200 kDa N-terminal heavy chain fragment. (See review by Kaufman, Transfusion Med. Revs. 6:235 (1992)).

Physiological activation of the heterodimer occurs through proteolytic cleavage of the protein chains by thrombin. Thrombin cleaves the heavy chain to a 90 kDa protein, and then to 54 kDa and 44 kDa fragments. Thrombin also cleaves the 80 kDa light chain to a 72 kDa protein. It is the latter protein, and the two heavy chain fragments (54 kDa and 44 kDa above), held together by calcium ions, that constitute active FVIII. Inactivation occurs when the 44 kDa A2 heavy chain fragment dissociates from the molecule or when the 72 kDa and 54 kDa proteins are further cleaved by thrombin, activated protein C or FXa. In plasma, FVIII is stabilized by association with a 50-fold molar excess of VWF protein ("VWF"), which appears to inhibit proteolytic destruction of FVIII as described above.

The amino acid sequence of FVIII is organized into three structural domains: a triplicated A domain of 330 amino acids, a single B domain of 980 amino acids, and a duplicated C domain of 150 amino acids. The B domain has no homology to other proteins and provides 18 of the 25 potential asparagine(N)-linked glycosylation sites of this protein. The B domain has apparently no function in coagulation and can be deleted with the B-domain deleted FVIII molecule still having procoagulatory activity.

The Factor VIII products on the market are currently presented as a lyophilized formulation of Factor VIII either produced by recombinant technology or purified from pooled plasma. The lyophilized product is reconstituted prior to administration. Once reconstituted, shelf-life of the Factor VIII is relatively short. Factor VIII is a relatively unstable protein, particularly in aqueous solutions. Stabilization during manufacturing and storage by complexing with other plasma proteins, particularly von Willebrand factor (vWF) and albumin, has been described. See, for example, U.S. Pat. No. 6,228,613. U.S. Pat. No. 5,565,427 discloses a stabilized formulation of Factor VIII comprising an amino acid or one of its salts or homologues and a detergent or an organic polymer such as polyethyleneglycol. U.S. Pat. No. 5,605,884 discloses stabilized formulations of Factor VIII in high ionic strength media based on histidine buffer in the presence of calcium chloride and a high concentration of sodium chloride or potassium chloride. Such compositions were shown to improve significantly the stability of Factor VIII in aqueous form following reconstitution. The importance of calcium ions in the formulations of Factor VIII is generally recognized. According to U.S. Pat. No. 6,599,724, the presence of other divalent cations, namely $Cu^{2+}$ and $Zn^{2+}$, optionally in the presence of $Ca^{2+}$ ions or $Mn^{2+}$ ions improves the stability of Factor VIII. Also WO 2011/027152 A1 describes stable aqueous Factor VIII compositions comprising various additives.

In view of the short shelf life of Factor VIII after reconstitution of a lyophilisate, there is a need for methods to increase the stability of reconstituted Factor VIII in aqueous solution. To provide a purified FVIII preparation with increased stability in the liquid phase is desirable for different reasons. First of all, it is of advantage to have a sufficient time span at ambient temperature to support manufacturing of the purified FVIII product at ambient temperature. In particular, the filling step necessitates some storage of a liquid bulk to increase flexibility in manufacturing. Secondly, an increased stability of the liquid purified FVIII would be of advantage for physician and patient if the product could not be applied directly after reconstitution. And finally, the use of FVIII under continuous infusion conditions e.g. upon surgery in hospitalized patients is depending on a preferably high product stability after reconstitution (Takedani H., Haemophilia 2010, 16: 740-746). A FVIII molecule with increased stability would also be an advantage for development of a FVIII preparation suitable for long term storage under liquid conditions.

The inventors of this application surprisingly found that the stability of purified Factor VIII after reconstitution of a lyophilisate is substantially enhanced in single-chain Factor VIII constructs. Such constructs can be obtained by preventing the proteolytic cleavage which typically occurs in the Golgi compartment prior to secretion of Factor VIII. The single-chain constructs exhibit a better stability in solution after purification and/or a better bioavailability upon subcutaneous administration.

SUMMARY OF THE INVENTION

In a first aspect the present invention relates to a method for increasing the stability of a Factor VIII molecule after purification, lyophilization and reconstitution, comprising preventing proteolytic cleavage of the Factor VIII molecule into a first fragment comprising essentially the A1 domain and the A2 domain and a second fragment comprising essentially the A3 domain, the C1 domain and the C2 domain.

The first aspect encompasses a method for increasing the stability of a Factor VIII molecule after purification, lyophilization and reconstitution, comprising preventing proteolytic cleavage of the Factor VIII molecule into a first fragment comprising essentially the A1 domain and the A2 domain and a second fragment comprising essentially the A3 domain, the C1 domain and the C2 domain throughout manufacturing of the Factor VIII molecule.

The first aspect further encompasses a method for increasing the stability of a Factor VIII molecule after purification, lyophilization and reconstitution, comprising preventing proteolytic cleavage of the Factor VIII molecule into a first fragment comprising essentially the A1 domain and the A2 domain and a second fragment comprising essentially the A3 domain, the C1 domain and the C2 domain prior to the purification of the Factor VIII molecule.

With regard to these methods according to the invention the terms "throughout manufacturing of the Factor VIII molecule" and "prior to the purification of the Factor VIII molecule" are intended to mean that the methods of the invention prevent the cleavage of Factor VIII into a first fragment comprising essentially the A1 domain and the A2 domain and a second fragment comprising essentially the A3 domain, the C1 domain and the C2 domain but the methods according to the invention do not prevent the activation cleavage of Factor VIII which may occur after administration of the reconstituted Factor VIII molecule. The Factor VIII molecules generated by the methods of the invention can still be activated by thrombin which cleaves the Factor VIII molecule after Arg 372, Arg 740 and Arg 1689.

In a second aspect, the present invention relates to a method for increasing the stability of a Factor VIII molecule after purification, lyophilization and reconstitution, comprising inactivating the proteolytic cleavage sites which are cleaved during secretion of said Factor VIII molecule by the host cell expressing the Factor VIII molecule except the cleavage site between the signal sequence and the mature Factor VIII. Typically, at least 50% of the Factor VIII molecules expressed and secreted by the host cells are single-chain Factor VIII molecules. Preferably, at least 60%, or at least 70%, or at least 80%, or at least 90%, or at least 95% of the Factor VIII molecules expressed and secreted by the host cells are single-chain Factor VIII molecules.

Preferably, the method comprises inactivating the proteolytic cleavage site between Arg1648 and Glu1649 and, if present in the FVIII molecule, the proteolytic cleavage site between Arg1313 and Ala1314. The inactivation of the proteolytic cleavage site may be effected by deleting one or more residues of the protease recognition sequence. For example, inactivation step may comprise deleting at least Arg1648 from the Factor VIII sequence. In one embodiment, the inactivation step comprises deleting at least the amino acid sequence from Arg1313 to Arg1648 from the Factor VIII sequence.

In another embodiment of the first aspect of the invention the inactivation of the proteolytic cleavage site is effected by substituting one or more amino acid residues forming the protease recognition sequence.

In yet another embodiment (concerning those FVIII variants which retain the part of the B-domain comprising Arg1313) the method further comprises inactivating the proteolytic cleavage site between Arg1313 and Ala1314 by deletion or substitution of one or more residues forming the protease recognition sequence. In a particularly preferred embodiment, the method comprises deleting at least a portion from the Factor VIII amino acid sequence which comprises both protease cleavage sites after residues Arg1313 and Arg1648.

It is further preferred that a first amino acid selected from the amino acids at positions 741 to 1647 of the Factor VIII sequence is fused with a second amino acid selected from the amino acids at positions 1649 to 1690 of the Factor VIII sequence, whereby the proteolytic cleavage site between Arg1648 and Glu1649 and, if present in the FVIII molecule, the cleavage site between Arg1313 and Ala1314 is inactivated.

In another preferred embodiment the Factor VIII molecule stabilized in accordance with the first or second aspect of the invention exhibits an increased stability in aqueous solution. The loss of activity of the modified Factor VIII molecule, in aqueous solution, after storage for 7 days at 25° C. is preferably less than 15%.

In another preferred embodiment the Factor VIII molecule stabilized in accordance with the first or second aspect of the invention exhibits an increased stability in aqueous solution after reconstitution.

In yet another preferred embodiment the Factor VIII molecule stabilized in accordance with the first or second aspect of the invention exhibits an increased bioavailability after non-intravenous injection, as compared to the bioavailability of human wild type Factor VIII or as compared to a B-domain deleted Factor VIII molecule where Asn745 is fused to Pro1640, administered at the same dose and in the same manner. In yet another preferred embodiment the Factor VIII molecule stabilized in accordance with the first or second aspect of the invention exhibits an increased bioavailability after non-intravenous injection, as compared to the bioavailability of a B-domain deleted Factor VIII molecule where Asn745 is fused to Pro1640, administered at the same dose and in the same manner. The bioavailability of the modified FVIII is preferably increased by at least 25%, as compared to the bioavailability of human wild type Factor VIII or of a B-domain deleted Factor VIII molecule where Asn745 is fused to Pro1640, each administered at the same dose and in the same manner. In another preferred embodiment the non-intravenous injection is subcutaneous, transdermal or intramuscular injection.

Another preferred embodiment is a method wherein (i) the Factor VIII exhibits improved plasma half-life after intravenous administration relative to human wild type Factor VIII; preferably wherein the plasma half-life is improved by at least 40% relative to human wild type Factor VIII, or (ii) wherein the Factor VIII exhibits a longer time period for the thrombin peak level as determined in a thrombin generation assay over time in hemophilia A mice to fall below 50 nM after intravenous administration relative to human wild type Factor VIII; preferably wherein this time period is prolonged by at least 10 hours relative to human wild type Factor VIII, or (iii) wherein the Factor VIII retains a higher activity as determined by a one-stage FVIII:C assay after having been incubated for 4 days in human plasma at 37° C. relative to human wild type Factor VIII after having been incubated for 4 days in human plasma at 37° C.; preferably wherein the retained activity of the Factor VIII is at least 10% higher relative to that of a human wild type Factor VIII after having been incubated for 4 days in human plasma at 37° C.

The methods may further comprise the steps of
(i) providing a nucleic acid encoding a modified Factor VIII molecule in which the proteolytic cleavage sites between Arg1648 and Glu1649, and between Arg1313 and Ala1314, are inactivated,
(ii) transforming a host cell with said nucleic acid,
(iii) culturing the transformed host cell under conditions such that the modified Factor VIII molecule is expressed, and
(iv) recovering the modified Factor VIII molecule from the host cells or from the culture medium.

In another aspect, the present invention relates to a method for improving the bioavailability of a Factor VIII molecule after non-intravenous administration, comprising inactivating the proteolytic cleavage site between Arg1648 and Glu1649 and, if present in the FVIII molecule, the proteolytic cleavage site between Arg1313 and Ala1314. Preferably, the non-intravenous injection is subcutaneous injection. The bioavailability after subcutaneous injection is preferably increased by at least 25% as compared to that of human wild type Factor VIII or of a B-domain deleted Factor VIII molecule where Asn745 is fused to Pro1640, each administered at the same dose and in the same manner.

In another aspect, the present invention relates to a method for improving the plasma half-life of a Factor VIII molecule after intravenous administration relative to human wild-type Factor VIII, comprising inactivating the proteolytic cleavage site between Arg1648 and Glu1649, and, if present in the FVIII molecule, the proteolytic cleavage site between Arg1313 and Ala1314.

In another aspect, the present invention relates to a method for prolonging the time period for the thrombin peak level as determined in a thrombin generation assay over time in hemophilia A mice to fall below 50 nM after intravenous administration of a Factor VIII molecule relative to human wild type Factor VIII, comprising inactivating the proteolytic cleavage site between Arg1648 and Glu1649, and, if present in the FVIII molecule, the proteolytic cleavage site between Arg1313 and Ala1314.

In another aspect, the present invention relates to a method for retaining a higher activity for a Factor VIII molecule as determined by a one-stage FVIII:C assay after having been incubated for 4 days in human plasma at 37° C. relative to human wild type Factor VIII after having been incubated for 4 days in human plasma at 37° C., comprising inactivating the proteolytic cleavage site between Arg1648 and Glu1649, and, if present in the FVIII molecule, the proteolytic cleavage site between Arg1313 and Ala1314.

A preferred embodiment of the methods described above are methods wherein a first amino acid selected from the amino acids at positions 741 to 1647 of the Factor VIII sequence is fused with a second amino acid selected from the amino acids at positions 1649 to 1690 of the Factor VIII sequence, whereby the proteolytic cleavage site between Arg1648 and Glu1649, and, if present in the FVIII molecule, the proteolytic cleavage site between Arg1313 and Ala1314 is inactivated.

The preferred embodiments of the different aspects are applicable mutatis mutandis.

In yet another aspect, the present invention relates to a pharmaceutical preparation comprising a single chain Factor VIII molecule for use in the treatment or prophylaxis of a bleeding disorder, preferably hemophilia A, by (i) on the one hand non-intravenous administration, wherein the bioavailability of said single chain Factor VIII molecule is increased by at least 25% as compared to human wild type Factor VIII or as compared to a B-domain deleted human Factor VIII molecule where Asn745 is fused to Pro1640, administered at the same dose and in the same manner, or (ii) on the other hand by intravenous administration, wherein (a) the plasma half-life of said single chain Factor VIII molecule after intravenous administration is increased by at least 40%, relative to human wild type Factor VIII, administered at the same dose and in the same manner, or (b) the single chain Factor VIII molecule exhibits a time period prolonged by at least 10 hours for the thrombin peak level as determined in a thrombin generation assay over time in hemophilia A mice to fall below 50 nM after intravenous administration relative to human wild type Factor VIII, administered at the same dose and in the same manner.

In yet another aspect, the present invention relates to a pharmaceutical preparation comprising a single chain Factor VIII molecule for use in the treatment or prophylaxis of a bleeding disorder, preferably hemophilia A, wherein the single chain Factor VIII molecule retains at least a 10% higher activity as determined by a one-stage FVIII:C assay after having been incubated for 4 days in human plasma at 37° C. relative to human wild type Factor VIII after having been incubated for 4 days in human plasma at 37° C.

In yet another aspect, the present invention relates to a pharmaceutical preparation comprising a single chain Factor VIII molecule for use in the treatment or prophylaxis of a bleeding disorder, preferably hemophilia A, by non-intravenous administration, wherein the dose of said FVIII molecule can be decreased by at least 25% as compared to that of a B-domain deleted Factor VIII molecule where Asn745 is fused to Pro1640, administered at the same dose and in the same manner to achieve the same hemostatic activity in blood.

In another aspect, the present invention relates to the use of a single chain Factor VIII molecule for achieving an increased stability after reconstitution or a longer shelf life of a pharmaceutical preparation for treating a bleeding disorder, wherein (i) the Factor VIII activity of the pharmaceutical preparation comprising the single chain Factor VIII molecule, after reconstitution and storage at room temperature for 7 days after reconstitution is at least 10% higher than that of a pharmaceutical preparation comprising the same amount of a B-domain deleted Factor VIII molecule where Asn745 is fused to Pro1640, or (ii) wherein the single chain Factor VIII molecule retains at least a 10% higher activity as determined by a one-stage FVIII:C assay when incubated for 4 days in human plasma at 37° C. relative to human wild type Factor VIII after having been incubated for 4 days in human plasma at 37° C. at the same concentration.

DESCRIPTION OF THE DRAWINGS

FIG. 9 depicts the domain structure of mature human factor VIII.

DETAILED DESCRIPTION

Figure 1:
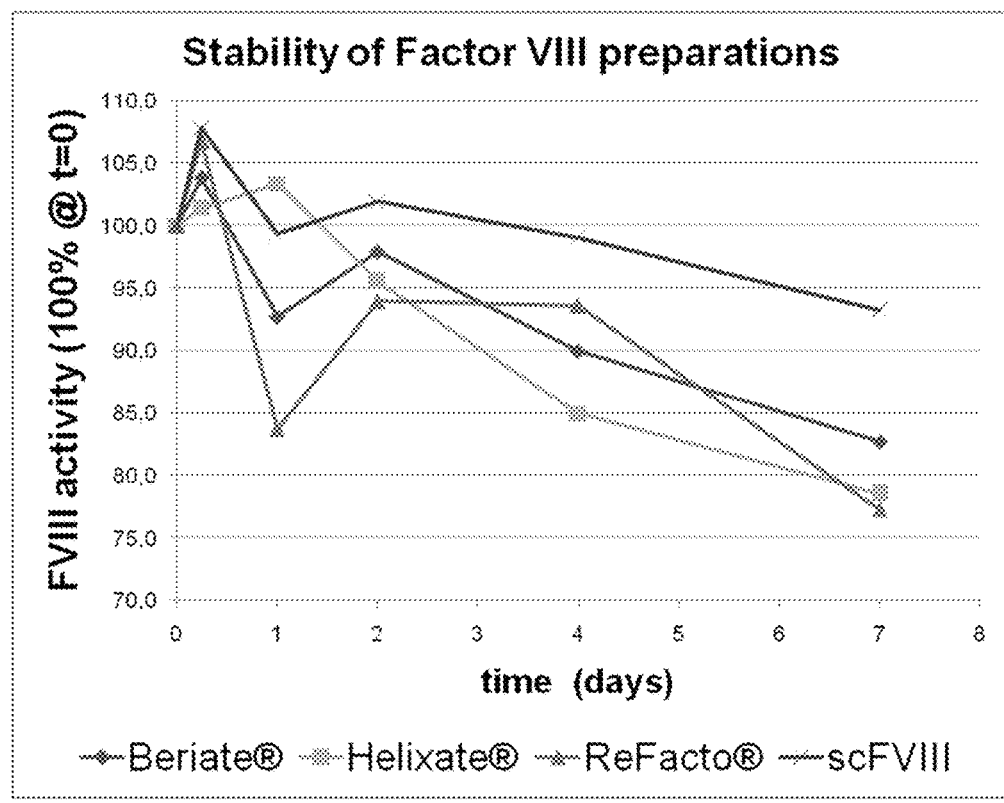
FIG. 1 depicts the results of Example 1. Various Factor VIII molecules have been provided as aqueous solutions, and their stability has been monitored over a time period of seven days. The loss in activity after seven days of storage is much less for the single chain Factor VIII molecule as compared to heterodimeric (two-chain) full length Factor VIII molecules (Beriate® and Helixate®) and to heterodimeric (two-chain) B-domain deleted constructs (ReFacto®).

The present invention relates to a method for increasing the stability of a Factor VIII molecule after purification, lyophilization and reconstitution, comprising preventing proteolytic cleavage of the Factor VIII molecule into a first fragment comprising essentially the A1 domain and the A2 domain and a second fragment comprising essentially the A3 domain, the C1 domain and the C2 domain.

This invention further pertains to a method for increasing the stability of a Factor VIII molecule after purification, lyophilization and reconstitution, comprising inactivating the proteolytic cleavage site between Arg1648 and Glu1649 and, optionally inactivating the proteolytic cleavage site between Arg1313 and Ala1314, if present in the Factor VIII molecule.

Factor VIII

The terms "blood coagulation Factor VIII", "Factor VIII" and FVIII" are used interchangeably herein. Mature human Factor VIII consists of 2332 amino acids which are arranged in the following domains and have the domain structure depicted in FIG. 9: A1 (residues 1-336), A2 (residues 373-710), B (residues 741-1648), A3 (residues 1690-2019), C1 (residues 2020-2172), and C2 (residues 2173-2332).

In addition, there are three acidic regions a1 (337-372), a2 (711-740), and a3 (1649-1689). It is known that the acidic region a3 is involved in the binding of the Factor VIII molecule to von Willebrand Factor (vWF) which plays an important role in blood coagulation. During secretion, the FVIII is cleaved between the B-domain and the a3 acidic region, resulting in a heterodimeric polypeptide The factor VIII heterodimer consists of a light chain (comprising A3, C1 and C2) and a variably sized heavy chain (comprising A1, A2 and B). The latter is heterogeneous due to limited proteolysis within the B-domain. In case of heterodimeric B-domain deleted constructs the "heavy chain" comprises A1 and A2 but lacks part or all of the B-domain.

The amino acid sequence of the mature wild type form of human blood coagulation Factor VIII is shown in SEQ ID NO:2. The reference to an amino acid position of a specific sequence means the position of said amino acid in the FVIII wild-type protein and does not exclude the presence of mutations, e.g. deletions, insertions and/or substitutions at other positions in the sequence referred to. For example, a mutation in "Glu2004" referring to SEQ ID NO:2 does not exclude that in the modified homologue one or more amino acids at positions 1 through 2332 of SEQ ID NO:2 are missing. A DNA sequence encoding SEQ ID NO:2 is shown in SEQ ID NO:1.

"Blood coagulation Factor VIII" includes wild type blood coagulation Factor VIII as well as derivatives of wild type blood coagulation Factor VIII having the procoagulant activity of wild type blood coagulation Factor VIII. Derivatives may have deletions, insertions and/or additions compared with the amino acid sequence of wild type Factor VIII. Preferred derivatives are FVIII molecules in which all or part of the B-domain has been deleted. Amino acid positions indicated throughout this application always refer to the position of the respective amino acid in the full length mature (i.e. after signal peptide cleavage) wild-type FVIII.

The term "factor VIII" includes any factor VIII variants or mutants having at least 10%, preferably at least 25%, more preferably at least 50%, most preferably at least 75% of the biological activity of wild type factor VIII. A suitable test to determine the biological activity of Factor VIII is the one stage or the two stage coagulation assay (Rizza et al. 1982. Coagulation assay of FVIII:C and FIXa in Bloom ed. The Hemophilias. NY Churchchill Livingston 1992) or the chromogenic substrate FVIII:C assay (S. Rosen, 1984. Scand J Haematol 33: 139-145, suppl.). The content of these references is incorporated herein by reference.

As non-limiting examples, Factor VIII molecules include Factor VIII mutants preventing or reducing APC cleavage (Amano 1998. Thromb. Haemost. 79:557-563), albumin-fused FVIII molecules (WO 2011/020866 A2), FVIII-Fc fusion molecules (WO 04/101740 A), Factor VIII mutants further stabilizing the A2 domain (WO 97/40145), FVIII mutants resulting in increased expression (Swaroop et al. 1997. JBC 272:24121-24124), Factor VIII mutants with reduced immunogenicity (Lollar 1999. Thromb. Haemost. 82:505-508), FVIII reconstituted from differently expressed heavy and light chains (Oh et al. 1999. Exp. Mol. Med. 31:95-100), FVIII mutants reducing binding to receptors leading to catabolism of FVIII like HSPG (heparan sulfate proteoglycans) and/or LRP (low density lipoprotein receptor related protein) (Ananyeva et al. 2001. TCM, 11:251-257), disulfide bond-stabilized FVIII variants (Gale et al., 2006. J. Thromb. Hemost. 4:1315-1322), FVIII mutants with improved secretion properties (Miao et al., 2004. Blood 103:3412-3419), FVIII mutants with increased cofactor specific activity (Wakabayashi et al., 2005. Biochemistry 44:10298-304), FVIII mutants with improved biosynthesis and secretion, reduced ER chaperone interaction, improved ER-Golgi transport, increased activation or resistance to inactivation and improved half-life (summarized by Pipe 2004. Sem. Thromb. Hemost. 30:227-237), and FVIII mutants having a deletion of all or part of the B-domain (see, e.g., WO 2004/067566 A1, WO 02/102850 A2, WO 00/24759 A1 and U.S. Pat. No. 4,868,112). All of these factor VIII mutants and variants are incorporated herein by reference in their entirety.

The term "single-chain Factor VIII" refers to a Factor VIII molecule which has not been proteolytically cleaved into two chains (e.g. a heavy chain and a light chain) during secretion from the cells expressing said FVIII molecule and, accordingly, is present as a single polypeptide chain.

Preventing Cleavage

The method of the invention comprises preventing proteolytic cleavage of the Factor VIII molecule into a first fragment comprising essentially the A1 domain and the A2 domain and a second fragment comprising essentially the A3 domain, the C1 domain and the C2 domain. The term "preventing proteolytic cleavage" includes partially preventing proteolytic cleavage and completely preventing proteolytic cleavage. It further includes the embodiment "reducing proteolytic cleavage". In other words, "preventing proteolytic cleavage of the Factor VIII molecule" does not require completely abolishing any proteolytic cleavage such that substantially 100% of the Factor VIII molecules expressed and secreted by the host cells are single chain molecules (though this embodiment is encompassed by the method of the invention). Usually, the proteolytic cleavage of the Factor VIII molecule is prevented in a manner such that at least 50%, preferably at least 60%, more preferably at least 70%, more preferably at least 80%, more preferably at least 90%, most preferably at least 95% of the Factor VIII molecules expressed and secreted by the host cells are single chain molecules. The incomplete prevention of cleavage may, at least in part, be due to the fact that there can be some minor cleavage sites within the B domain which can lead to proteolytic cleavage of a small portion of the Factor VIII molecules even if the major cleavage sites (at R1313 and R1648) are absent. This minor cleavage may or may not be prevented in accordance with this invention.

The first fragment comprises essentially the A1 domain and the A2 domain of Factor VIII. The first fragment may comprise the A1 domain and the A2 domain, each domain having exactly the amino acid sequence indicated above. For example, the first fragment may comprise at least amino acids 1 to 740 of the amino acid sequence of SEQ ID NO:2. Alternatively, the first fragment may comprise a variant of this sequence, having amino acid deletions, substitutions and/or insertions which do not substantially affect the Factor VIII activity. The first fragment may additionally comprise an N-terminal part of the B domain of Factor VIII.

The second fragment comprises essentially the A3 domain, the C1 domain and the C2 domain. The second fragment may comprise the A3 domain, the C1 domain and the C2 domain, each domain having exactly the amino acid sequence indicated above. For example, the second fragment may comprise at least amino acids 1690 to 2332 of the amino acid sequence shown in SEQ ID NO:2. Alternatively, the second fragment may comprise a variant of this sequence, having amino acid deletions, substitutions and/or insertions which do not substantially affect the Factor VIII activity. The second fragment may additionally comprise a C-terminal part of the acidic a3 region.

The method of the invention comprises preventing the proteolytic cleavage during secretion of the recombinantly expressed FVIII molecule, which would result in a heterodimeric (two-chain) polypeptide. That is, the method includes obtaining a single-chain Factor VIII molecule. This can be achieved in various ways, e.g. by inactivating the proteolytic cleavage sites involved in the intracellular processing of the mature, one-chain FVIII into the heterodimeric FVIII eventually secreted by the host cells.

In one embodiment the step of inactivating the proteolytic cleavage site between Arg1648 and Glu1649 comprises deleting one or more amino acids forming the protease recognition sequence. The cleavage site after residue 1648 is a furin-type cleavage site. The recognition sequence for the protease in the Factor VIII sequence is LKRHQR. Preferably, the inactivation step comprises deleting one, two, three, four, five or more of these amino acid residues forming the recognition sequence. Preferably, the inactivation step comprises deleting at least one basic amino acid within the recognition sequence, more preferably, the inactivation step comprises deleting at least the arginine at position 1648. Still more preferably, the inactivation step comprises deleting at least amino acids 1643 to 1648 of the Factor VIII sequence. If the respective FVIII derivative comprises Arg1313, the inactivation step comprises also deleting at least the arginine at position Arg 1313. Still preferably is deleting at least amino acids 1313 to 1648 of the Factor VIII sequence to inactivate both cleavage sites after 1313 and 1648, respectively.

Most preferably, the inactivation step comprises deleting at least the amino acid sequence from residues 800 to 1648 from the Factor VIII sequence, e.g. the amino acid sequence from residues 741 to 1648 from the Factor VIII sequence. In another preferred embodiment, a first amino acid selected from the amino acids at positions 741 to 1647 of the Factor VIII sequence is fused with a second amino acid selected from the amino acids at positions 1649 to 1690 of the Factor VIII sequence, whereby the proteolytic cleavage during secretion is prevented. Preferred deletions are as follows:

amino acid 740 is fused to amino acid 1650, whereby amino acids 741 to 1649 are deleted;

amino acid 740 is fused to amino acid 1690, whereby amino acids 741 to 1689 are deleted;
amino acid 740 is fused to amino acid 1669, whereby amino acids 741 to 1668 are deleted;
amino acid 743 is fused to amino acid 1650, whereby amino acids 744 to 1649 are deleted;
amino acid 764 is fused to amino acid 1650, whereby amino acids 765 to 1649 are deleted;
amino acid 764 is fused to amino acid 1653, whereby amino acids 765 to 1652 are deleted;
amino acid 764 is fused to amino acid 1656, whereby amino acids 765 to 1655 are deleted;
amino acid 745 is fused to amino acid 1650, whereby amino acids 746 to 1649 are deleted;
amino acid 745 is fused to amino acid 1653, whereby amino acids 746 to 1652 are deleted;
amino acid 745 is fused to amino acid 1656, whereby amino acids 746 to 1655 are deleted;
amino acid 757 is fused to amino acid 1650, whereby amino acids 758 to 1649 are deleted;
amino acid 757 is fused to amino acid 1653, whereby amino acids 758 to 1652 are deleted;
amino acid 757 is fused to amino acid 1656, whereby amino acids 758 to 1655 are deleted;
amino acid 793 is fused to amino acid 1649, whereby amino acids 794 to 1648 are deleted;
amino acid 793 is fused to amino acid 1690, whereby amino acids 794 to 1689 are deleted;
amino acid 747 is fused to amino acid 1649, whereby amino acids 748 to 1648 are deleted;
amino acid 751 is fused to amino acid 1649, whereby amino acids 752 to 1648 are deleted;
amino acid 776 is fused to amino acid 1649, whereby amino acids 777 to 1648 are deleted;
amino acid 770 is fused to amino acid 1667, whereby amino acids 771 to 1666 are deleted.

The molecules resulting from the deletion are usually obtained in the form of single chain Factor VIII molecules.

Preferred single chain FVIII molecules have a deletion of all or part of the B-domain and a deletion of all or a part of the acidic a3 region, so that the cleavage site at Arg1648 (which is usually cleaved during secretion) is deleted. Single chain FVIII molecules are disclosed in, e.g., WO 2004/067566 A1; US 2002/132306 A1; Krishnan et al. (1991) European Journal of Biochemistry vol. 195, no. 3, pages 637-644; Herlitschka et al. (1998) Journal of Biotechnology, vol. 61, no. 3, pages 165-173; Donath et al. (1995) Biochem. J., vol. 312, pages 49-55. These single-chain Factor VIII molecules described in these references are incorporated herein by reference.

The fusions referred to above may be direct fusions or indirect fusions. In the latter case, the deleted amino acids are replaced by a heterologous spacer. This embodiment is described in more detail hereinafter. It is possible that the deleted amino acids are replaced with a peptidic linker consisting of about 1 to about 500 amino acids, or about 2 to 250 amino acids, or about 3 to about 100 amino acids, or about 4 to about 50 amino acids, or about 5 to about 10 amino acids. The peptidic linker should be flexible and not immunogenic (Robinson et al.; PNAS (1998), Vol 95, p 5929). The peptidic linkers may consist of Gly preceded N-terminally to said Gly by multimers of the amino acid sequence GlyGlySer or GlyGlySerSer or any combination thereof, in a specific embodiment the peptidic linker consists of 80 to 120 amino acids.

In an alternative embodiment, one or more amino acids which form the protease recognition site at residue 1313 and 1648 may be substituted with another amino acid such that the cleavage does not occur. For example, the basic amino acids may be replaced with hydrophobic amino acids.

Preparation of Single-Chain Factor VIII

The step of "preventing proteolytic cleavage" or "inactivating a proteolytic cleavage site" is carried out prior to the purification, lyophilisation and reconstitution of the Factor VIII. The step of "preventing proteolytic cleavage" or "inactivating a proteolytic cleavage site" is typically carried out during the preparation of the Factor VIII molecule. The method of the invention may include preventing the proteolytic cleavage during expression of the Factor VIII molecule (in host cells), or inactivating the proteolytic cleavage site at Arg1313 and/or Arg1648 during the preparation of the nucleic acid encoding the Factor VIII molecule.

These steps of "preventing proteolytic cleavage" or "inactivating a proteolytic cleavage site" may include removing, from a nucleic acid encoding Factor VIII, a portion encoding the proteolytic cleavage site at Arg1313 and/or Arg1648, in accordance with the embodiments described above. This typically results in a nucleic acid encoding single chain Factor VIII. Generally, the method of the invention may further include providing a nucleic acid encoding the single-chain Factor VIII, e.g. in an expression plasmid or vector.

The nucleic acid, the expression vector or the expression plasmid may then be introduced into host cells, preferably mammalian host cells, for expression. The method of the invention may further comprise culturing the host cells under suitable conditions such that the modified Factor VIII molecule, e.g. the single chain Factor VIII molecule, is expressed; and optionally recovering (e.g. purifying) the modified Factor VIII molecule from the host cells or from the culture medium. Generally, techniques of manipulating the nucleic acid encoding Factor VIII, of culturing mammalian cells to allow expression of the Factor VIII, and of purifying Factor VIII from the cell culture medium are known in the art.

It is preferred to purify the single chain Factor VIII molecule to 80% purity, more preferably ≥95% purity and particularly preferred is a pharmaceutically pure state that is greater than 99.9% pure with respect to contaminating macromolecules, particularly other proteins or/and nucleic acids, and free of infectious and pyrogenic agents. Preferably, an isolated or purified modified Factor VIII molecule is substantially free of other polypeptides.

The methods of the invention may further comprise the steps of purifying, lyophilizing, and reconstituting the single chain Factor VIII. The reconstitution is preferably carried out by using water, e.g. "water for injection".

Stability

The Factor VIII molecules prepared in accordance with the present invention exhibit enhanced stability relative to full length Factor VIII and/or relative to a B-domain deleted Factor VIII molecule where Asn745 is fused to Pro1640 (i.e. a B-domain deleted Factor VIII molecule consisting essentially of amino acids 1-745 and 1640-2332 of SEQ ID NO:2).

As used herein, the term "stability" refers to stability in aqueous solution, preferably to stability in aqueous solution after reconstitution of a lyophilized Factor VIII preparation, e.g. by adding water to the lyophilized Factor VIII preparation. Typically, the lyophilized Factor VIII preparation is reconstituted with "water for injection".

The stability in aqueous solution can be determined by providing the Factor VIII molecule in aqueous solution and incubating it for a certain period of time. In a preferred embodiment, the conditions for determining the storage stability of the Factor VIII molecule are as follows:

The Factor VIII molecule is provided in aqueous solution having the following composition:

| | |
|---|---|
| L-histidine | 25 mM |
| NaCl | 225 mM |
| calcium chloride | 4 mM |
| Tween ® 80 | 0.03% (w/w) |
| sucrose | 2% (w/w) |
| D-mannitol | 8% (w/w) |
| pH 7.0. | |

This solution is referred to hereinafter as "Buffer A". The initial Factor VIII activity in the aqueous solution is preferably between 100 IU/ml and 1,500 IU/ml, preferably it is 100 IU/ml.

The so prepared Factor VIII solution can then be incubated at 25° C. for at least 24 hours, preferably for at least two days, more preferably for at least five days, most preferably for seven or eight days. After the incubation period the stability is determined by measuring the Factor VIII activity in the solution, preferably by using a chromogenic substrate assay (e.g. Coamatic® Factor VIII, Chromogenix). The lower the loss in activity relative to the initial activity, the higher is the stability of the Factor VIII molecule. Most preferably, the stability is determined as in Example 1 or 2 below.

According to the present invention the loss in Factor VIII activity of the single-chain Factor VIII after seven days of storage under the above-identified conditions is less than 15%, preferably less than 12%, most preferably less than 10%.

Typically, the initial Factor VIII activity at the start of the incubation period (t=0) is normalized to 100%. The remaining Factor VIII activity after 24 hours of storage in Buffer A at 25° C. is preferably at least 95% of the initial Factor VIII activity. The remaining Factor VIII activity after 48 hours of storage in Buffer A at 25° C. is preferably at least 95% of the initial Factor VIII activity. The remaining Factor VIII activity after 4 days of storage in Buffer A at 25° C. is preferably at least 90%, more preferably at least 95% of the initial Factor VIII activity. The remaining Factor VIII activity after 7 days of storage in Buffer A at 25° C. is preferably at least 85%, more preferably at least 90%, most preferably at least 95% of the initial Factor VIII activity. The remaining Factor VIII activity after 8 days of storage in Buffer A at 25° C. is preferably at least 85%, more preferably at least 90%, most preferably at least 95% of the initial Factor VIII activity.

The remaining Factor VIII activity of the single chain Factor VIII is usually higher than that of two-chain Factor VIII molecules (assuming that both molecules have been incubated under identical conditions for the same period of time).

The term "human full length two-chain Factor VIII" is used herein interchangeably with the term "human wild-type Factor VIII".

In one embodiment, the remaining Factor VIII activity of the single chain Factor VIII is higher than that of human full length two-chain Factor VIII. In another embodiment, the remaining Factor VIII activity of the single chain Factor VIII is higher than that of a B-domain deleted Factor VIII molecule where Asn745 is fused to Pro1640 (i.e. a B-domain deleted Factor VIII molecule consisting essentially of amino acids 1-745 and 1640-2332 of SEQ ID NO:2).

Preferably, the remaining Factor VIII activity of the single chain Factor VIII after 48 hours of storage in Buffer A at 25° C. exceeds the remaining Factor VIII activity of human full length two-chain Factor VIII by at least 4 percentage points. It is also preferred that the remaining Factor VIII activity of the single chain Factor VIII after 48 hours of storage in Buffer A at 25° C. exceeds the remaining Factor VIII activity of a B-domain deleted Factor VIII molecule where Asn745 is fused to Pro1640 (i.e. a B-domain deleted Factor VIII molecule consisting essentially of amino acids 1-745 and 1640-2332 of SEQ ID NO:2) by at least 4 percentage points.

In another embodiment, the remaining Factor VIII activity of the single chain Factor VIII after 4 days of storage in Buffer A at 25° C. exceeds the remaining Factor VIII activity of human full length two-chain Factor VIII by at least 5 percentage points. It is also preferred that the remaining Factor VIII activity of the single chain Factor VIII after 4 days of storage in Buffer A at 25° C. exceeds the remaining Factor VIII activity of a B-domain deleted Factor VIII molecule where Asn745 is fused to Pro1640 (i.e. a B-domain deleted Factor VIII molecule consisting essentially of amino acids 1-745 and 1640-2332 of SEQ ID NO:2) by at least 5 percentage points.

In another embodiment, the remaining Factor VIII activity of the single chain Factor VIII after 7 days of storage in Buffer A at 25° C. exceeds the remaining Factor VIII activity of human full length two-chain Factor VIII by at least 5, preferably by at least 10 percentage points. It is also preferred that the remaining Factor VIII activity of the single chain Factor VIII after 7 days of storage in Buffer A at 25° C. exceeds the remaining Factor VIII activity of a B-domain deleted Factor VIII molecule where Asn745 is fused to Pro1640 (i.e. a B-domain deleted Factor VIII molecule consisting essentially of amino acids 1-745 and 1640-2332 of SEQ ID NO:2) by at least 5, preferably by at least 10 percentage points.

In another embodiment, the remaining Factor VIII activity of the singe chain Factor VIII after 8 days of storage in Buffer A at 25° C. exceeds the remaining Factor VIII activity of human full length two-chain Factor VIII by at least 5, preferably by at least 10 percentage points. It is also preferred that the remaining Factor VIII activity of the single chain Factor VIII after 8 days of storage in Buffer A at 25° C. exceeds the remaining Factor VIII activity of a B-domain deleted Factor VIII molecule where Asn745 is fused to Pro1640 (i.e. a B-domain deleted Factor VIII molecule consisting essentially of amino acids 1-745 and 1640-2332 of SEQ ID NO:2) by at least 5, preferably by at least 10 percentage points.

Alternatively to Buffer A other buffers may also be used like, for example the buffer used in Example 2 of the present invention.

The preferred pH range for the buffers of the present invention is a pH range from 5.5 to 9.0, preferably a pH range from 6.0 to 8.5 and especially preferred a pH range from 6.5 to 8.0.

The activity of Factor VIII can be determined by a chromogenic or clotting assay, or any other bioassay. Preferably, the Factor VIII activity is determined as shown in Example 1 below.

Bioavailability

In another embodiment, the Factor VIII molecule stabilized in accordance with the present invention exhibits improved bioavailability after non-intravenous injection, as compared to two chain human wild type Factor VIII or compared to two chain human B-domain deleted Factor VIII. The non-intravenous injection is preferably subcutaneous, transdermal or intramuscular injection. Most preferably, the non-intravenous injection is subcutaneous injection.

The term "bioavailability", as used herein, refers to the proportion of an administered dose of a Factor VIII or a FVIII-related preparation that can be detected in plasma at predetermined times until a final time point after subcutaneous, intravenous or intradermal administration. Typically, bioavailability is measured in test animals by administering a dose of between 10 and 1000 IU/kg of the preparation (e.g. 400 IU/kg body weight); obtaining plasma samples at predetermined time points after administration; and determining the content of the Factor VIII or Factor VIII-related polypeptides in the samples using one or more of a chromogenic or clotting assay (or any bioassay), an immunoassay, or an equivalent thereof. The bioavailability is expressed as the area under the curve (AUC) of the concentration or activity of the coagulation factor in plasma on the y-axis and the time after administration on the x-axis until a predefined final time point after administration. Preferably, this predefined time point is 72 or 48 hours after administration. Most preferably, the bioavailability is determined as shown in Example 3 herein below. Relative bioavailability of a test preparation refers to the ratio between the AUC of the test preparation (here: single chain Factor VIII) and that of the reference preparation (e.g. full length recombinant two-chain Factor VIII or two-chain B-domain deleted Factor VIII) which is administered in the same dose and way (e.g. intravenous, subcutaneous or intradermal) as the test preparation.

According to the present invention, the bioavailability of the single chain Factor VIII after subcutaneous injection is higher than that of the two-chain human wild type Factor VIII or of two-chain human B-domain deleted Factor VIII. Preferably, the bioavailability (AUC over 72 hours after subcutaneous injection) is increased by at least 10%, more preferably by at least 25%, more preferably by at least 50%, most preferably by at least 75%, relative to wild type FVIII. In another embodiment, the bioavailability (AUC over 72 hours after subcutaneous injection) is increased by at least 10%, more preferably by at least 20%, more preferably by at least 30%, most preferably by at least 40%, relative to a B-domain deleted Factor VIII molecule where Asn745 is fused to Pro1640 (i.e. a B-domain deleted Factor VIII molecule consisting essentially of amino acids 1-745 and 1640-2332 of SEQ ID NO:2).

Improvement of Plasma Half-Life (In-Vivo)

In another embodiment, the Factor VIII molecule stabilized in accordance with the present invention exhibit increased pharmacokinetic (PK) parameters.

Factor VIII molecules of the invention can be tested by i.v. injection into different species like hemophilia A mice or cynomolgus monkeys e.g. at a dose of 100 IU/kg or 250 IU/kg respectively e.g. as determined in a chromogenic assay. Blood samples are drawn at various time points after administration e.g. until 72 hours (hrs) in hemophilia A mice and e.g. until 24 hrs in cynomolgus monkeys. Citrate plasma is prepared immediately and used for quantification of FVIII:C e.g. by a chromogenic assay system (FVIII:C) (Chromogenix—Instrumentation Laboratory SpA, Milan, Italy).

The AUC of the FVIII levels in plasma is calculated using the linear trapezoidal rule to calculate $AUC_{last}$: from t=0 to last observation. Terminal half-life ($t_{1/2\beta}$) is determined by a log-linear regression using the points of the terminal phase selected by the adjusted R2 criterion. AUC: from t=0 to infinity (extrapolated by using the regression model of the terminal phase).

The single chain FVIII molecules according to the invention show at least a 40%, preferably at least a 50%, even more preferably at least a 60% increased terminal half life as compared to the terminal half-life a human wild-type Factor VIII administered at the same dose and in the same manner.

Preferably the plasma half-life is determined as shown in Example 5.

Prolongation of Efficacy as Determined in a Thrombin Generation Assay (In-Vivo)

In another embodiment, the Factor VIII molecule stabilized in accordance with the present invention exhibit a longer time period for the thrombin peak level as determined in a thrombin generation assay over time in hemophilia A mice to fall below 50 nM after intravenous administration relative to human wild type Factor VIII. This test show that also the functionality of FVIII is stabilized in the molecules according to the invention.

FVIII molecules according to the invention can be tested by first administering the FVIII molecule of the invention at an equimolar dose (e.g. at 250 IU/kg) intravenously into hemophilia A mice. At different time points (e.g. daily from day 1 to 8) citrated blood is collected and a thrombin generation assay (TGA) is performed e.g. by calibrated thrombinography (CAT) (Thrombinoscope, Netherlands) after intrinsic activation in presence of Phospholipid (e.g. Rossix, Mölndal, Sweden)/Pathromtin® SL (Siemens Healthcare Diagnostics Products GmbH, Marburg, Germany) (1:30). Thrombin peak levels are recorded. The average AUC of peak thrombin levels from days 1-8 is calculated by the linear trapezoidal rule. The AUC of the two Factor VIII products are compared using an approximate F-test for the difference in AUC in a linear model with variable variances per time-point and treatment group resulting in a estimated time until peak levels of thrombin drop below a defined limit ranging of 50 nM.

Preferably the efficacy in a thrombin generation assay is determined as shown in Example 6.

In hemophilia A mice scFVIII shows a favorable hemostatic activity compared to human wild-type Factor VIII. This translates into an averaged at least 10 hrs longer, preferably at least 15 hours longer and even more preferred at least 20 hours longer thrombin generation activity value for scFVIII versus full-length rFVIII before the thrombin peak level falls below a level of 50 nM.

Retaining Higher FVIII:C Activity in Plasma (Ex Vivo)

In another embodiment, the Factor VIII molecule stabilized in accordance with the present invention retain a higher activity as determined by a one-stage FVIII:C assay after having been incubated for 4 days in human plasma at 37° C. relative to human wild type Factor VIII after having been incubated for 4 days in human plasma at 37° C.; preferably wherein the retained activity of the Factor VIII is at least 10% higher relative to that of a human wild type Factor VIII after having been incubated for 4 days in human plasma at 37° C.

Samples with Factor VIII molecules according to the invention can be tested by diluting them into with FVIII deficient plasma (e.g. from Siemens Healthcare Diagnostics) to 1 IU/mL FVIII:C (based on values determined by the chromogenic substrate assay). The FVIII-samples are then incubated at 37° C. for varying time periods (e.g. for 0, 0.25, 1, 2, 4 and 8 days) in presence of 0.05% Na-azide. After each incubation period, FVIII:C is then determined by a one-stage-coagulation assay e.g. by using Pathromtin-SL (Siemens Healthcare Diagnostics) as activator, normalized to the value at t=0 (% FVIII:C) and plotted versus the incubation time.

After a 4 day incubation at 37° C. the Factor VIII molecule of the invention has retained at least a 10% higher FVIII:C activity, preferably at least 15% higher FVIII:C activity, preferably at least a 20% higher FVIII:C activity, preferably at least a 25% higher FVIII:C activity, preferably at least a 30% higher FVIII:C activity.

Preferably the activity in plasma is determined as shown in Example 4.

Treatment and Prophylaxis

The single-chain Factor VIII constructs in accordance with the present invention having increased stability after reconstitution can be administered in the treatment or prophylaxis of bleeding disorders.

As used herein, the term "bleeding disorders" includes familial and acquired hemophilia A and B, familial or acquired von Willebrand disease, familial or acquired deficiency of any coagulation factor, all types of trauma, blunt or penetrating, leading to severe hemorrhage either from a single organ, a bone fraction or from polytrauma, bleeding during surgical procedures including perk or postoperative haemorrhage, bleeding due to cardiac surgery including patients undergoing extracorporal circulation and hemodilution in pediatric cardiac surgery, intracerebral hemorrhage, subarachnoid hemorrhage, sub- or epidural bleeding, bleedings due to blood loss and hemodilution, by non-plasmatic volume substitution leading to reduced levels of coagulation factors in affected patients, bleedings due to disseminated intravascular coagulation (DIC) and a consumption coagulopathy, thrombocyte dysfunctions, depletion and coagulopathies, bleeding due to liver cirrhosis, liver dysfunction and fulminant liver failure, liver biopsy in patients with liver disease, bleeding after liver and other organ transplantations, bleeding from gastric varices and peptic ulcer bleeding, gynaecological bleedings as dysfunctional uterine bleeding (DUB), premature detachment of the placenta, periventricular haemorrhage in low birth weight children, post partum haemorrhage, fatal distress of newborns, bleeding associated with burns, bleeding associated with amyloidosis, hematopoietic stem cell transplantation associated with platelet disorder, bleedings associated with malignancies, infections with haemorrhaging viruses, bleeding associated with pancreatitis.

The components of the pharmaceutical preparation may be dissolved in conventional physiologically compatible aqueous buffer solutions to which there may be added, optionally, pharmaceutical excipients to provide the pharmaceutical preparation. The components of the pharmaceutical preparation may already contain all necessary pharmaceutical, physiologically compatible excipients and may be dissolved in water for injection to provide the pharmaceutical preparation.

Such pharmaceutical carriers and excipients as well as the preparation of suitable pharmaceutical formulations are well known in the art (see for example "Pharmaceutical Formulation Development of Peptides and Proteins", Frokjaer et al., Taylor & Francis (2000) or "Handbook of Pharmaceutical Excipients", 3$^{rd}$ edition, Kibbe et al., Pharmaceutical Press (2000)). In certain embodiments, a pharmaceutical composition can comprise at least one additive such as a bulking agent, buffer, or stabilizer. Standard pharmaceutical formulation techniques are well known to persons skilled in the art (see, e.g., 2005 Physicians' Desk Reference®, Thomson Healthcare: Montvale, N.J., 2004; Remington: The Science and Practice of Pharmacy, 20th ed., Gennaro et al., Eds. Lippincott Williams & Wilkins: Philadelphia, Pa., 2000). Suitable pharmaceutical additives include, e.g., sugars like mannitol, sorbitol, lactose, sucrose, trehalose, or others, amino acids like histidine, arginine, lysine, glycine, alanine, leucine, serine, threonine, glutamic acid, aspartic acid, glutamine, asparagine, phenylalanine, or others, additives to achieve isotonic conditions like sodium chloride or other salts, stabilizers like Polysorbate 80, Polysorbate 20, Polyethylene glycol, propylene glycol, calcium chloride, or others, physiological pH buffering agents like Tris(hydroxymethyl)aminomethan, and the like. In certain embodiments, the pharmaceutical compositions may contain pH buffering reagents and wetting or emulsifying agents. In further embodiments, the compositions may contain preservatives or stabilizers. In particular, the pharmaceutical preparation comprising the blood coagulation factor may be formulated in lyophilized or stable soluble form. The blood coagulation factor may be lyophilized by a variety of procedures known in the art. Lyophilized formulations are reconstituted prior to use by the addition of one or more pharmaceutically acceptable diluents such as sterile water for injection or sterile physiological saline solution or a suitable buffer solution.

The composition(s) contained in the pharmaceutical preparation of the invention may be delivered to the individual by any pharmaceutically suitable means. Various delivery systems are known and can be used to administer the composition by any convenient route. Preferably, the composition(s) contained in the pharmaceutical preparation of the invention are delivered to the individual by non-intravenous injection. More preferably, the composition(s) of the invention are formulated for subcutaneous, intramuscular, intraperitoneal, intracerebral, intrapulmonar, intranasal, intradermal or transdermal administration, most preferably for subcutaneous, intramuscular or transdermal administration according to conventional methods. The formulations can be administered continuously by infusion or by bolus injection. Some formulations may encompass slow release systems.

The composition(s) of the pharmaceutical preparation of the present invention is/are administered to patients in a therapeutically effective dose, meaning a dose that is sufficient to produce the desired effects, preventing or lessening the severity or spread of the condition or indication being treated without reaching a dose which produces intolerable adverse side effects. The exact dose depends on many factors as e.g. the indication, formulation, mode of administration and has to be determined in preclinical and clinical trials for each respective indication.

In one embodiment of the invention, the plasma level of the coagulation factor in the treated subject is, during a period from 5 hours after injection to 8 hours after non-intravenous injection, continuously higher than 2%, preferably higher than 5%, more preferably higher than 8%, most preferably higher than 10%, of the normal plasma level of the coagulation factor in healthy subjects. The plasma level is to be determined as shown hereinafter in Example 3.

In one embodiment of the invention, the plasma level of the coagulation factor in the treated subject is, during a period from 4 hours after injection to 16 hours after non-intravenous injection, continuously higher than 2%, preferably higher than 5%, more preferably higher than 8%, most preferably higher than 10%, of the normal plasma level of the coagulation factor in healthy subjects.

In another embodiment of the invention, the plasma level of the coagulation factor in the treated subject is, during a period from 3 hours after injection to 24 hours after non-intravenous injection, continuously higher than 2%, preferably higher than 4%, more preferably higher than 6%, most preferably higher than 8%, of the normal plasma level of the coagulation factor in healthy subjects.

In another embodiment of the invention, the plasma level of the coagulation factor in the treated subject is, during a period from 2 hours after injection to 32 hours after non-intravenous injection, continuously higher than 2%, preferably higher than 3%, more preferably higher than 4%, most preferably higher than 5%, of the normal plasma level of the coagulation factor in healthy subjects.

Preferably, the dose of single-chain Factor VIII for one non-intravenous injection is less than 1,000 IU/kg body weight, or less than 800 IU/kg body weight, or less than 600 IU/kg body weight, or less than 400 IU/kg body weight, e.g. at a dose of from about 10 IU/kg body weight to about 1,000 IU/kg body weight, or from about 20 IU/kg body weight to about 800 IU/kg body weight, or from about 30 IU/kg body weight to about 700 IU/kg body weight, or from about 40 IU/kg body weight to about 600 IU/kg body weight, or from about 50 IU/kg body weight to about 500 IU/kg body weight, or from about 75 IU/kg body weight to about 400 IU/kg body weight, or from about 100 IU/kg body weight to about 300 IU/kg body weight, or from about 50 IU/kg body weight to about 1,000 IU/kg body weight, or from about 50 IU/kg body weight to about 800 IU/kg body weight, or from about 50 IU/kg body weight to about 700 IU/kg body weight, or from about 50 IU/kg body weight to about 600 IU/kg body weight, or from about 50 IU/kg body weight to about 500 IU/kg body weight, or from about 50 IU/kg body weight to about 400 IU/kg body weight, or from about 50 IU/kg body weight to about 300 IU/kg body weight, or about 50 IU/kg body weight to about 200 IU/kg body weight. The FVIII can be administered on its own, or as a complex with VWF.

The pharmaceutical composition(s) of the invention may be administered alone or in conjunction with other therapeutic agents. These agents may be incorporated as part of the same pharmaceutical.

EXAMPLES

Example 1: Stability of Purified Factor VIII Molecules after Reconstitution

The following Factor VIII preparations were used in this Example:

Beriate®, a lyophilized human coagulation Factor VIII concentrate, was obtained from CSL Behring GmbH. Beriate® comprises plasma-derived Factor VIII in heterodimeric form.

Helixate®, a lyophilized, recombinant coagulation Factor VIII was obtained from CSL Behring GmbH, Helixate® contains recombinantly produced heterodimeric Factor VIII.

ReFacto® is a lyophilized Factor VIII preparation containing heterodimeric, B-domain-deleted Factor VIII produced by recombinant technology. It can be obtained from, e.g., Pfizer Pharma GmbH, Germany.

Beriate®, Helixate®, and ReFacto® are predominantly heterodimeric two-chain polypeptides.

The construct termed "scFVIII" is a single-chain Factor VIII produced by recombinant expression in mammalian cell culture cells. The single-chain Factor VIII used in this Example was obtained by directly fusing Asn764 with Thr1653, and provided in lyophilized form after purification.

That is, "scFVIII" is a single chain polypeptide consisting substantially of amino acids 1-764 and 1653-2332 of SEQ ID NO:2.

Beriate®, Helixate®, and ReFacto® were reconstituted according the manufacturer's instructions as given in the package insert. "scFVIII" was reconstituted by dissolving the purified and lyophilized FVIII preparation in water for injection resulting in a composition containing 25 mM L-histidine, 225 mM NaCl, 4 mM $CaCl_2$, 0.03% Tween 80, 2% sucrose, 8% D-mannitol, pH 7.0.

The reconstituted FVIII products were incubated at 25° C. The FVIII activity of the products was determined in duplicates by a chromogenic substrate assay (Coamatic® Factor VIII, Chromogenix) at the following time points: 0 h, 6 h, 1 day, 2 days, 4 days, 7 days. Activity values were normalized to time point 0.

The results are shown in the following Table and in FIG. 1.

TABLE 1

| | Factor VIII activity over time | | | | | |
|---|---|---|---|---|---|---|
| | Time (days) | | | | | |
| | 0 d | 0.25 d | 1 d | 2 d | 4 d | 7 d |
| Beriate ® | 100.0 | 103.8 | 92.7 | 97.9 | 90.0 | 82.7 |
| Helixate ® | 100.0 | 101.4 | 103.3 | 95.5 | 85.0 | 78.6 |
| ReFacto ® | 100.0 | 106.7 | 83.7 | 94.0 | 93.6 | 77.3 |
| scFVIII | 100.0 | 107.8 | 99.4 | 102.0 | 99.0 | 93.3 |

As can be seen, "scFVIII" shows the lowest loss in activity and, consequently, is the most stable Factor VIII molecule.

Example 2: Stability of Purified Factor VIII Molecules after Reconstitution

The following Factor VIII preparations were used in this Example:

ReFacto® and "scFVIII" were the same as used in Example 1, with the difference that "scFVIII", provided by CSL Behring GmbH, was applied in a formulation containing different excipients. Advate® is a full-length, heterodimeric, recombinant Factor VIII preparation which was purchased in lyophilized form from Baxter.

Advate® and ReFacto® were reconstituted according the manufacturer's instructions as given in the package insert. "scFVIII" was reconstituted in water for injection resulting in a composition containing 20 mM L-histidine, 280 mM NaCl, 3.4 mM $CaCl_2$, 0.02% Tween 80, 0.6% sucrose, pH 7.0. The sample "scFVIII 001" had an initial FVIII activity of 100 IU/ml, the sample "scFVIII 0006" had an initial FVIII activity of 400 IU/ml. The reconstituted FVIII products were incubated at 25° C. The FVIII activity of the products was determined in duplicates by a chromogenic substrate assay (Coamatic® Factor VIII, Chromogenix) at the following time points: 0 h, 6 h, 1 day, 2 days, 4 days, 8 days. Activity values were normalized to time point 0.

Figure 2:
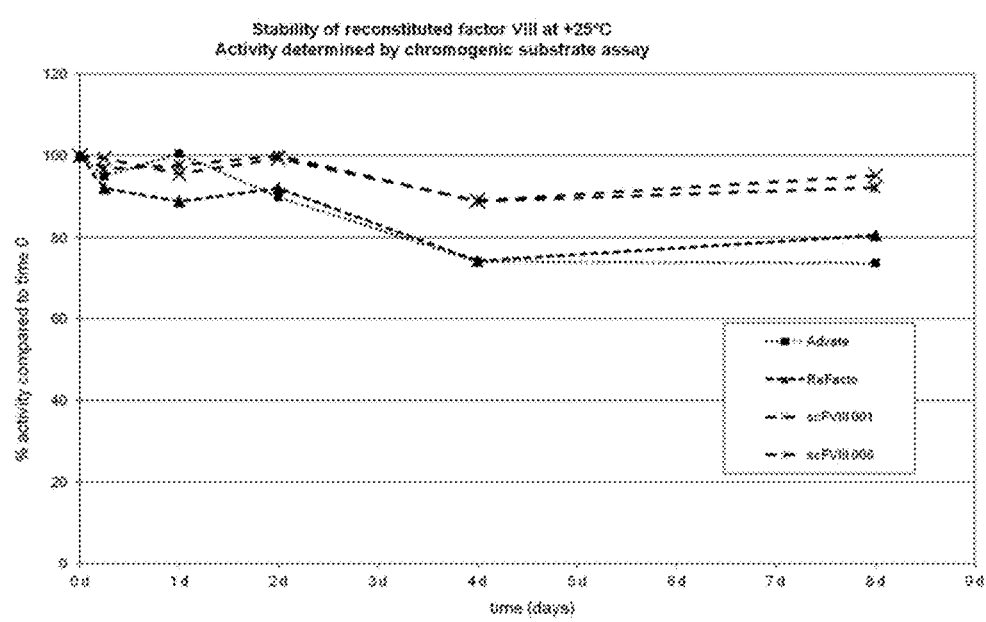
FIG. 2 depicts the results of Example 2. Various lyophilized Factor VIII preparations were reconstituted to aqueous solutions, and their stability has been monitored over a time period of seven days. The loss in activity after seven days of storage is much less for the single chain Factor VIII molecule as compared to a heterodimeric (two-chain) full length Factor VIII molecule (Advate®) and to a heterodimeric (two-chain) and B-domain deleted construct (ReFacto®).

The results are shown in the following Table and in FIG. 2.

TABLE 2

Factor VIII activity over time

| | Time (days) | | | | |
|---|---|---|---|---|---|
| | 0 d | 0.25 d | 1 d | 2 d | 4 d | 8 d |
| Advate | 100.0 | 94.9 | 100.6 | 89.8 | 74.1 | 73.7 |
| ReFacto | 100.0 | 92.0 | 88.8 | 92.1 | 74.3 | 80.6 |
| scFVIII 001 | 100.0 | 99.2 | 95.6 | 99.2 | 89.0 | 95.1 |
| scFVIII 006 | 100.0 | 96.8 | 97.6 | 100.0 | 88.9 | 92.3 |

As can be seen, "scFVIII" shows the lowest loss in activity and, consequently, is the most stable Factor VIII molecule.

Example 3: Bioavailability of Factor VIII Molecules

Advate®, ReFacto® and "scFVIII" were the same as used in Example 2 and reconstituted as described in Example 2.

Factor VIII knockout mice were used as animal model for hemophilia A. These mice lack exons 16 and 17 and thus do not express FVIII (Bi L. et al, Nature genetics, 1995, Vol 10(1), 119-121; Bi L. et al, Blood, 1996, Vol 88(9), 3446-3450). This allows the analysis of FVIII levels following treatment by quantification of FVIII activity in the plasma of the ko mice.

To assess whether extravascular injections might be an option for an improved therapy with human FVIII, subcutaneous injection was chosen. The design of the non-clinical pharmacokinetic study performed is detailed in table 3 below. Plasma levels of Factor VIII activity were determined following a single subcutaneous injection of the respective FVIII preparation (detailed treatment groups in table 3) to a hemophilia A model.

Corresponding groups were treated with the same dose of FVIII:chromogen activity. For a single application the Factor VIII was provided in a volume of 200 μL (identical volumes for all groups) prior to subcutaneous application to FVIII knockout (ko) mice weighing about 25 g. The treatment groups are summarized in table 3.

Under short term anesthesia, blood samples were drawn, anticoagulated using sodium citrate to 10% citrate blood, processed to plasma and stored at −70° C. for the determination of FVIII activity. The sampling time points are detailed in table 4. Quantification of FVIII activity in plasma was performed by a standard, aPTT based approach (Behring Coagulation Timer). The animals were kept at standard housing conditions.

TABLE 3

Treatment groups

| No. | Treatment | FVIII: chromogen/ Additive Dose | volume [mL/kg] | schedule | route | N |
|---|---|---|---|---|---|---|
| 1 | Advate ® | 400 IU/kg | 8 | single injection (t = 0) | s.c. | 25 |
| 2 | ReFacto ® | 400 IU/kg | 8 | single injection (t = 0) | s.c. | 25 |
| 3 | "scFVIII" | 400 IU/kg | 8 | single injection (t = 0) | s.c. | 20 |

Results

Figure 3:
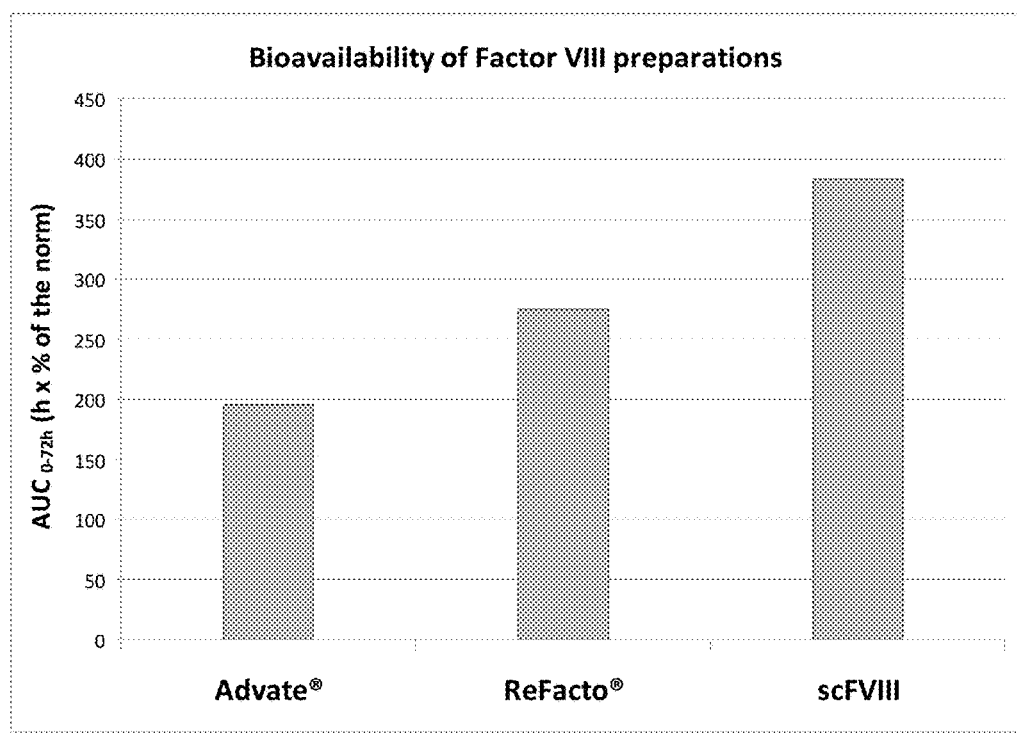
FIG. 3 depicts the results of Example 3. Three different Factor VIII molecules have been injected subcutaneously in mice and their bioavailability has been determined as described in Example 2. The bioavailability of the single chain Factor VIII molecule is substantially higher than that of a two chain and full length Factor VIII (Advate®) or a heterodimeric (two chain) B-domain deleted construct (ReFacto®).
Figure 4:
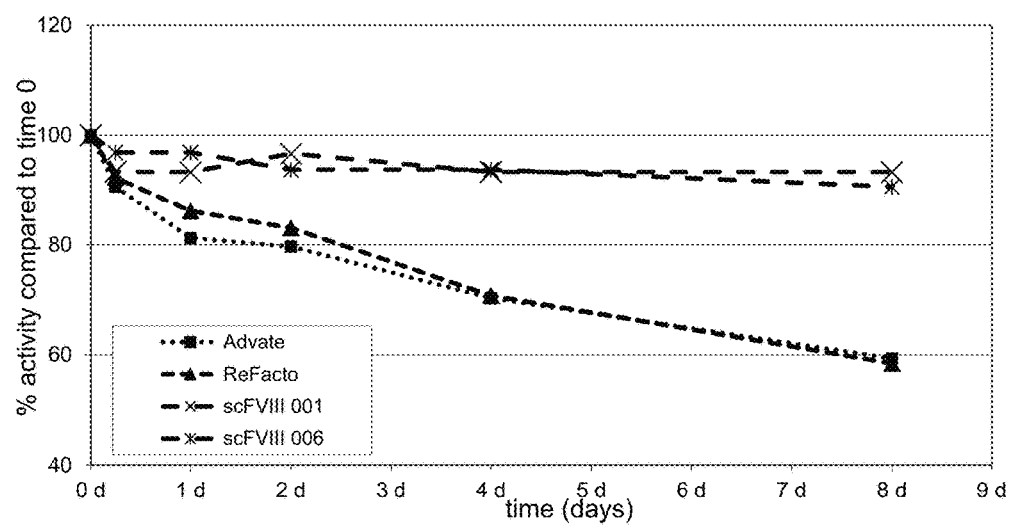
FIG. 4 depicts the results of Example 4. The Factor VIII molecule of the invention and 2 commercially obtainable FVIII preparations were incubated at 37° C. after purification, lyophilization and reconstitution. The FVIII-samples were incubated at 37° C. for varying time periods (0, 0.25, 1, 2, 4 and 8 days) and the FVIII:C activity was determined by an one-stage-coagulation assay. The values shown represent the average and standard deviation of two samples (except 0.25 days only one sample).

The results are summarized in Table 4 and FIG. 3.

TABLE 4

| timepoint | scFVIII | | | ReFacto ® | | | Advate ® | | |
|---|---|---|---|---|---|---|---|---|---|
| [hours] | mean | SD | n | mean | SD | n | mean | SD | n |
| 1 | 5.83 | 1.84 | 5 | 6.35 | 7.62 | 5 | 3.82 | 3.30 | 5 |
| 4 | 11.53 | 5.35 | 5 | 4.77 | 3.47 | 5 | 3.16 | 2.72 | 5 |
| 8 | 20.03 | 9.91 | 5 | 9.81 | 6.06 | 5 | 5.52 | 3.92 | 5 |
| 16 | 7.75 | 4.78 | 5 | 4.91 | 1.98 | 5 | 2.77 | 2.10 | 5 |
| 24 | 3.00 | 3.25 | 5 | 0.66 | 0.69 | 5 | 0.31 | 0.68 | 5 |
| 32 | 3.30 | 2.36 | 5 | 2.11 | 1.53 | 5 | 3.13 | 1.78 | 5 |
| 48 | 3.71 | 1.52 | 5 | 6.01 | 5.28 | 5 | 4.15 | 1.95 | 5 |
| 72 | 1.23 | 2.63 | 5 | 0.00 | 0.00 | 5 | 0.00 | 0.00 | 5 |
| $AUC_{0-72h}$ (h × % of the norm) | 383.9 | | | 275.1 | | | 195.1 | | |

Subcutaneous injection of 400 IU/kg single chain FVIII ("scFVIII") to FVIII ko mice resulted in a significant increase of FVIII activity in plasma level as compared to administration of heterodimeric full length FVIII (Advate®) or heterodimeric B-domain-deleted FVIII (ReFacto®). That is, the single chain Factor VIII molecule shows the highest in vivo bioavailability after subcutaneous injection into mice. The two chain full length construct Advate®, as well as the two chain B-domain deleted preparation ReFacto® showed substantially lower bioavailability.

Example 4: Stability of Factor VIII Molecules in Plasma (In-Vitro)

Different FVIII products (Advate®, ReFacto AF® and two lots of scFVIII as used in Example 2) were diluted with FVIII deficient plasma (Siemens Healthcare Diagnostics) to 1 IU/mL FVIII:C (based on values determined by the chromogenic substrate assay). The FVIII-samples were incubated at 37° C. for varying time periods (0, 0.25, 1, 2, 4 and 8 days) in presence of 0.05% Na-azide. After each incubation period, FVIII:C was determined by one-stage-coagulation assay using Pathromtin-SL (Siemens Healthcare Diagnostics) as activator, normalized to the value at t=0 (% FVIII:C) and plotted versus the incubation time. The values shown represent the average and standard deviation of two samples (except 0.25 days only one sample).

TABLE 5

Average % Activity Compared to Time 0

| | 0 d | 0.25 d | 1 d | 2 d | 4 d | 8 d |
|---|---|---|---|---|---|---|
| Advate | 100.00 | 90.63 | 81.25 | 79.69 | 70.31 | 59.38 |
| ReFacto | 100.00 | 92.31 | 86.15 | 83.08 | 70.77 | 58.46 |
| scFVIII 001 | 100.00 | 93.33 | 93.33 | 96.67 | 93.33 | 93.33 |
| scFVIII 006 | 100.00 | 96.88 | 96.88 | 93.75 | 93.75 | 90.63 |

Example 5: Stability of Factor VIII Molecules in Plasma (In-Vivo)

Figure 5:
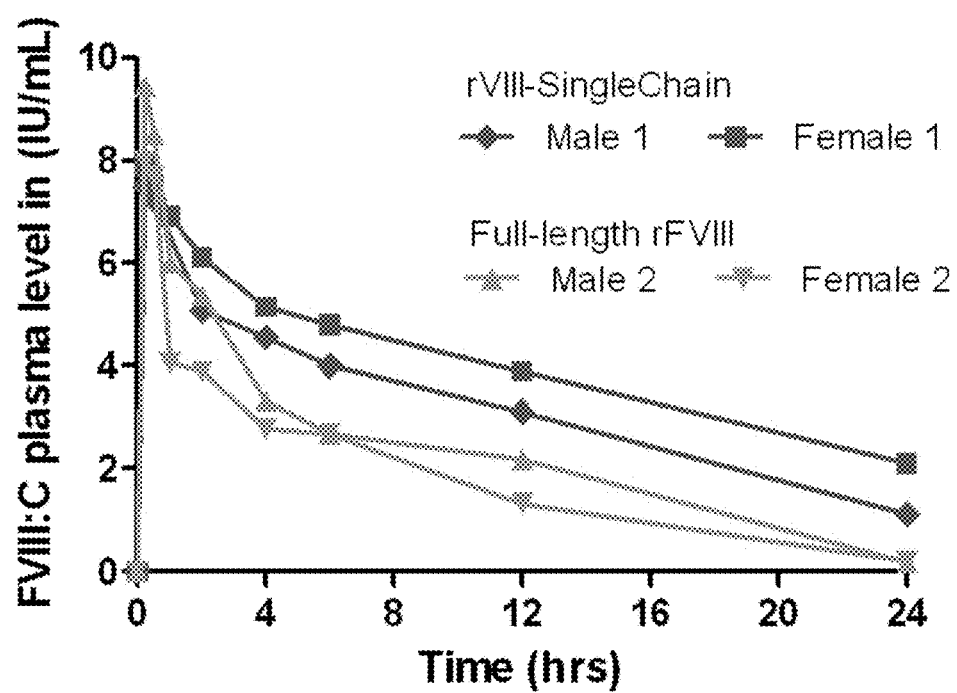
FIG. 5 depicts part of the results of Example 5. The pharmacokinetic (PK) profiles of scFVIII and full-length rFVIII (Advate®, Baxter Healthcare) were determined following a single I.V. injection to cynomolgus monkeys at a dose of 250 IU/kg.
Figure 6:
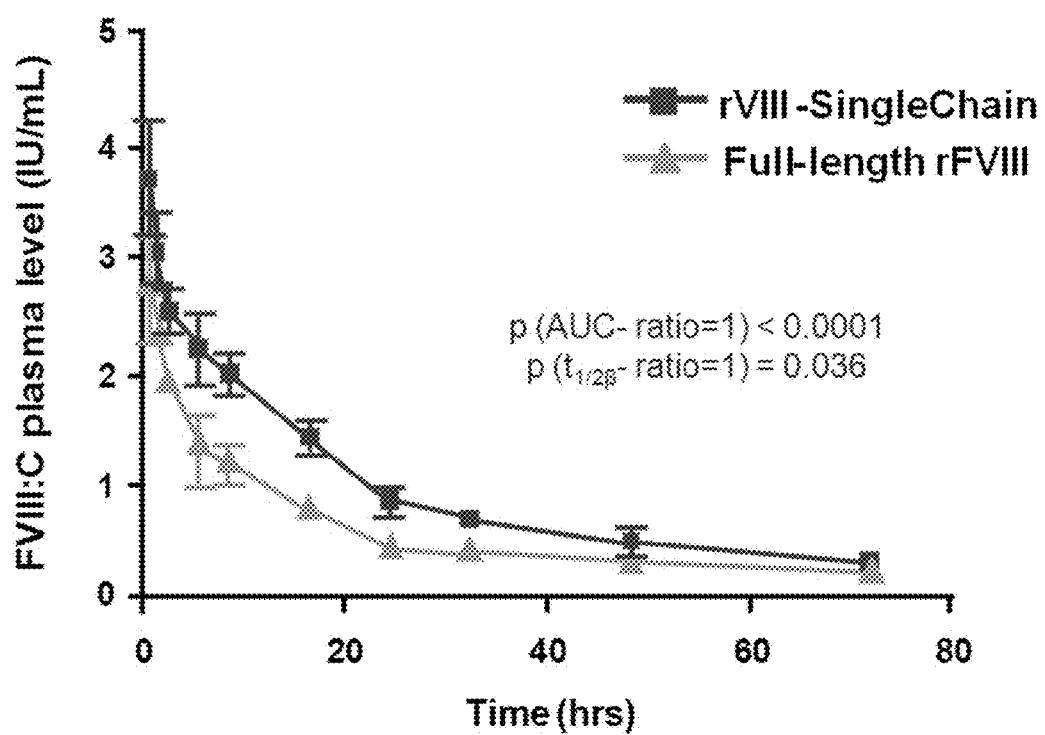
FIG. 6 depicts part of the results of Example 5. The pharmacokinetic (PK) profiles of full-length rFVIII (Advate®, Baxter Healthcare) were determined following a single I.V. injection to hemophilia A mice at a dose of 100 IU/kg.
Figure 7:
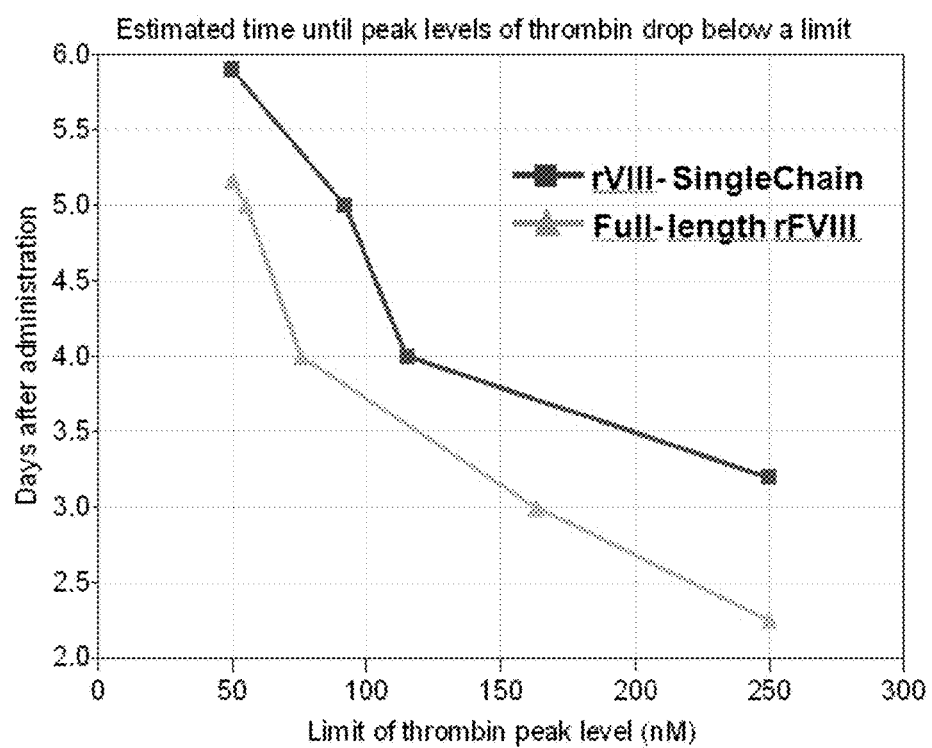
FIG. 7 depicts part of the results of Example 6. The average peak thrombin levels from days1-8 were determined after scFVIII or full-length rFVIII (Advate®, Baxter Healthcare) were administered to hemophilia A mice at a dose of 250 IU/kg.

The pharmacokinetic (PK) profiles of scFVIII and full-length rFVIII (Advate®, Baxter Healthcare) was determined following a single I.V. injection to cynomolgus monkeys (FIG. 5 and Table 6) and hemophilia A mice (FIG. 6 and Table 7) at doses of 250 IU/kg and 100 IU/kg, respectively. Test items were dosed according to labeled activity for Advate® and chromogenic activity (FVIII:C) for scFVIII. Blood samples were drawn predose (monkeys only) and at various time points after administration until 72 hours (hrs) in hemophilia A mice and until 24 hrs in cynomolgus monkeys. Citrate plasma was prepared immediately and used for quantification of FVIII:C by a chromogenic assay system (FVIII:C) (Chromogenix—Instrumentation Laboratory SpA, Milan, Italy).

The AUC of the FVIII levels in plasma was calculated using the linear trapezoidal rule to calculate $AUC_{last}$: from t=0 to last observation. Terminal half-life ($t_{1/2\beta}$) was determined by a log-linear regression using the points of the terminal phase selected by the adjusted R2 criterion. AUC: from t=0 to infinity (extrapolated by using the regression model of the terminal phase).

In cynomolgous monkeys scFVIII showed a ~1.6 fold enhanced $AUC_{0-tlast}$ or $t_{1/2\beta}$ with a correspondingly ~2 fold lower clearance (CL), while FVIII activity peak levels ($C_{max}$), representative of in vivo recovery (IVR), and volume of distribution at steady state ($V_{ss}$) appeared more similar versus full-length rFVIII. These PK parameter results were obtained from n=10 animals after toxicokinetic data from 8 additional monkeys, when dosed during the GLP-toxicity studies with 250 IU/kg of scFVIII, were included (Table 6 and FIG. 5).

In hemophilia A mice enhancement of $AUC_{0-tlast}$, of mean residence time (MRT), time until 5% FVIII activity trough levels, terminal half-life and a correspondingly lower CL ranged between 1.6-2 fold for scFVIII, while $C_{max}$, representative of IVR, and $V_{ss}$ appeared similar versus full-length rFVIII. $AUC_{0-tlast}$ and $t_{1/2\beta}$ results obtained after rVIII-SingleChain treatment were significantly better than for full-length rFVIII with an $AUC_{0-tlast}$ ratio of 1.97 (90% confidence interval (CI): 1.7-2.3; p-value (ratio=1): <0.0001), and a $t_{1/2\beta}$ ratio of 1.65 (90% CI: 1.11-2.70; p-value (ratio=1): 0.036 (Table 7 and FIG. 6).

TABLE 6

PK parameters of scFVIII and full-length rFVIII in cynomolgus monkeys

| Parameters | scFVIII (n = 10) | Full-length rFVIII (n = 2) |
|---|---|---|
| $AUC_{0-tlast}$ (hrs IU/mL) | 78.4 | 49.1 |
| $C_{max}$ (IU/mL) | 7.8 | 8.7 |
| CL ((mL/hrs)/kg) | 2.1 | 4.7 |
| $t_{1/2\beta}$ (hrs) | 11.0 | 6.8 |

TABLE 7

PK parameters of scFVIII and full-length rFVIII in hemophilia A mice

| Parameters | scFVIII | Full-length rFVIII |
|---|---|---|
| $AUC_{0-last}$ (hrs · IU/mL) | 35 | 18 |
| $C_{max}$ (IU/mL) | 2.3 | 2.2 |
| CL ((mL/hrs)/kg) | 2.7 | 5.5 |
| MRT (hrs) | 18 | 10 |
| $V_{SS}$ (mL/kg) | 50 | 57 |
| $t_{1/2\beta}$ (hrs) | 15.9 | 9.7 |
| Time until 0.05 IU/mL (hrs) | 73 | 39 |

Both sets of PK parameters reflect the increased stability of scFVIII after purification, lyophilization, reconstitution in vivo in plasma after administration to the two animal species tested.

Example 6: Thrombin Generation Assay in Hemophilia A Mice (Ex Vivo)

Citrate-(10% v/v) hemophilia A mouse blood was terminally collected under deep anesthesia at different time-points (days 1-8) when scFVIII or full-length rFVIII (Advate®), were dosed @ a level of 250 IU/kg. TGA was performed by calibrated thrombinography (CAT, Thrombinoscope, Netherlands) after intrinsic activation in presence of Phospholipid (Rossix, Mölndal, Sweden)/Pathromtin® SL (Siemens Healthcare Diagnostics Products GmbH, Marburg, Germany) (1:30). Thrombin peak levels were recorded. The average AUC of peak thrombin levels from days 1-8 was calculated by the linear trapezoidal rule. The AUC of the two Factor VIII products were compared using an approximate F-test for the difference in AUC in a linear model with variable variances per time-point and treatment group resulting in estimated time until peak levels of thrombin drop below a defined limit ranging between 50-250 nM.

Figure 8:
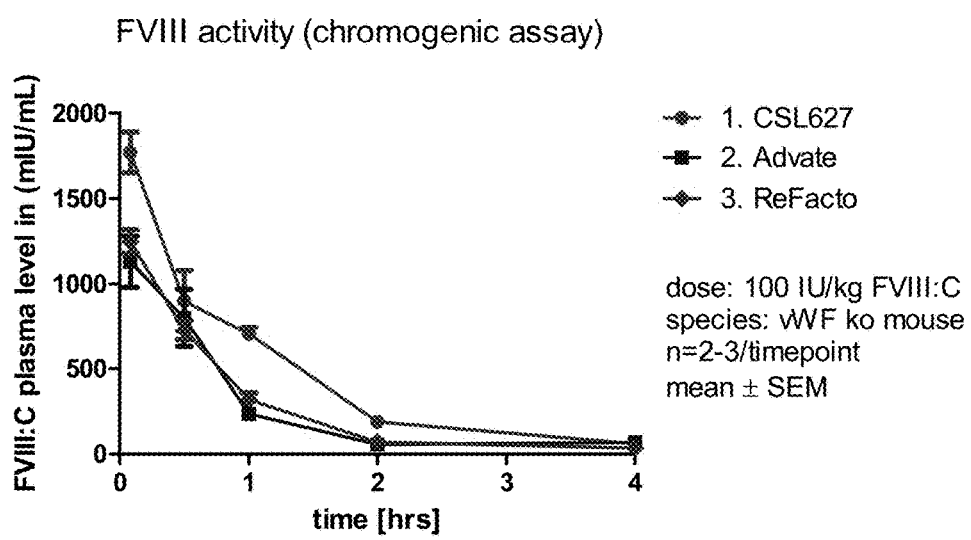
FIG. 8 depicts the results of Example 7. The pharmacokinetic (PK) profiles of full-length rFVIII (Advate®, Baxter Healthcare) and of a B-domain deleted Factor VIII (ReFacto®, Pfizer) was determined following a single I.V. injection to VWF deficient mice at a dose of 100 IU/kg.

In hemophilia A mice scFVIII showed a favorable hemostatic activity compared to full-length rFVIII as indicated by the estimated time until peak levels of thrombin drop below a defined limit ranging from 50-250 nm peak level (FIG. 8 and Table 8). This translated into an averaged 20 hrs longer thrombin generation activity value for scFVIII versus full-length rFVIII for the thrombin peak level interval between 50 and 250 nM. When assessing the area under the peak curve between days 1-8 the thrombin generation activity of scFVIII was significantly better with $p(AUC_{TGA\ Peak}$ ratio=1)=0.0002 (estimated ratio 1.26, 90% CI: 1.14-1.39) compared to full-length FVIII, or in other words it took significantly longer for scFVIII to fall below a thrombin peak level of 50 nm after administration than for the human wild-type Factor VIII Advate®.

These results again confirmed the increased functional stability of scFVIII after purification, lyophilization and reconstitution.

TABLE 8

Peak nm Thrombin

| time [hrs] | CSL627 (N = 8-14) | | Advate (N = 7-14) | |
|---|---|---|---|---|
| | mean | SD | mean | SD |
| 0 | 0 | 0 | 0 | 0 |
| 24 | 325.5 | 40.2 | 343.4 | 40.41 |
| 32 | 294 | 102.8 | 305.2 | 72.13 |
| 48 | 277.1 | 22.44 | 279.6 | 30.92 |
| 72 | 283.1 | 42.88 | 163.6 | 79.87 |
| 96 | 115.4 | 29.63 | 75.44 | 35.28 |

TABLE 8-continued

| | Peak nm Thrombin | | | |
|---|---|---|---|---|
| time | CSL627 (N = 8-14) | | Advate (N = 7-14) | |
| [hrs] | mean | SD | mean | SD |
| 120 | 91.85 | 57.63 | 55.17 | 30.89 |
| 144 | 45.6 | 36.15 | 24.61 | 13.52 |
| 168 | 8.453 | 12.66 | 14.13 | 19.44 |
| 192 | 3.901 | 9.384 | 4.71 | 8.1 |

Example 6: Stability of Factor VIII Molecules in vWF Deficient Plasma (In-Vivo)

scFVIII was reconstituted in 2.5 mL water for injection. ReFacto AF® and Advate® were reconstituted according to the description in the package insert. All test articles were aliquoted and stored immediately frozen at approximately −70° C. Prior to administration test articles were diluted with formulation buffer for CSL 627 to get a minimum practical volume ensuring a reliable administration.

12 VWF ko mice (6 female/6 male) per group received a single i.v. injection of 100 IU/kg of either scFVIII based on chromogenic FVIII activity and ReFacto AF® or Advate® based on the labeled FVIII activity into the lateral tail vein. Following administration of the different test items blood samples were drawn for determination of FVIII plasma levels at 0.083, 0.5, 1, 2, 4, 7, 16 and 24 hours from n=2-3 mice per time point. Blood samples were processed to 10% citrate (3.13% w/v) plasma and subsequently subjected to FVIII plasma level analysis using the chromogenic assays system The chromogenic FVIII activity was determined using the COAMATIC® FVIII test kit from Chromogenix, Italy.

The AUC of the FVIII levels in plasma was calculated using the linear trapezoidal rule to calculate AUClast: from t=0 to last observation.

Likewise to results obtained after i.v. administration to FVIII ko mice and normal monkeys as well as s.c. administration to FVIII ko mice analysis the exposure to CSL627 was higher compared to ReFacto AF® and Advate®. Since analysis of the AUC, the most relevant and representative PK parameter for systemic exposure yielded a 30% higher AUC value after administration of CSL627 compared to both ReFacto AF® and Advate®. Again, these observations reflect the increased intrinsic stability of scFVIII after purification, lyophilization, reconstitution in vivo in plasma after administration to mice lacking systemic, circulating VWF, hence in absence of its shielding and protective effect for systemic, circulating FVIII.

TABLE 9

Plasma levels of scFVIII compared to Advate ® and ReFacto AF ® after administration to VWF deficient mice at a dose level of 100 IU/kg

| | CSL627 | Advate ® | ReFacto AF ® |
|---|---|---|---|
| Baseline | 0.0 | 0.0 | 0.0 |
| Total Area | 2427 | 1654 | 1714 |
| Total Peak Area | 2427 | 1654 | 1714 |
| Number of Peaks | 1.000 | 1.000 | 1.000 |
| Peak 1 | | | |
| First X = | 0.0830 | 0.0830 | 0.0830 |
| Last X = | 24.00 | 24.00 | 24.00 |
| Peak X = | 0.0830 | 0.0830 | 0.0830 |
| Peak Y = | 1770 | 1131 | 1248 |
| Area under curve = | 2427 | 1654 | 1714 |
| % Area = | 100.0 | 100.0 | 100.0 |

The invention claimed is:

1. A method of treatment or prophylaxis for a bleeding disorder, comprising administering a modified Factor VIII molecule to a subject,
wherein the modified Factor VIII molecule comprises a Factor VIII molecule and a peptidic linker, wherein the Factor VIII molecule is modified by inactivating the proteolytic cleavage site between Arg1648 and Glu1649, and, if present in the Factor VIII molecule, the proteolytic cleavage site between Arg1313 and Ala1314, and
wherein the modified Factor VIII molecule is administered at a dosage of 20 IU/kg to 50 IU/kg, while retaining at least an equal or higher activity level of the Factor VIII molecule as compared to a higher dosage of an administered human wild-type Factor VIII molecule and/or an administered B-domain deleted human Factor VIII molecule in which Asn745 is fused to Pro1640.

2. The method of claim 1, wherein the modified FVIII is administered intravenously.

3. The method of claim 1, wherein the modified Factor VIII comprises SEQ ID NO: 2 modified to have a first amino acid selected from the amino acids at positions 741 to 1647 of SEQ ID NO: 2 indirectly fused to a second amino acid selected from the amino acids at positions 1649 to 1690 of SEQ ID NO: 2, deleting the intervening amino acids and replacing them with a peptidic linker, whereby the proteolytic cleavage site between Arg1648 and Glu1649, and, if present in the modified Factor VIII molecule, the proteolytic cleavage site between Arg1313 and Ala1314, is inactivated.

4. A method of treatment or prophylaxis for a bleeding disorder, comprising administering a modified Factor VIII molecule to a subject,
wherein the modified Factor VIII molecule comprises a Factor VIII molecule and a peptidic linker, wherein the Factor VIII molecule is modified by inactivating the proteolytic cleavage site between Arg1648 and Glu1649, and, if present in the Factor VIII molecule, the proteolytic cleavage site between Arg1313 and Ala1314, and
wherein the modified Factor VIII molecule is administered at a dosage of 20 IU/kg to 50 IU/kg, while at least maintaining or prolonging a thrombin peak level as compared to a higher dosage of an administered human wild-type Factor VIII molecule and/or an administered B-domain deleted human Factor VIII molecule in which Asn745 is fused to Pro1640.

5. The method of claim 4, wherein the modified FVIII is administered intravenously.

6. The method of claim 4, wherein the modified Factor VIII comprises SEQ ID NO: 2 modified to have a first amino acid selected from the amino acids at positions 741 to 1647 of SEQ ID NO: 2 indirectly fused to a second amino acid selected from the amino acids at positions 1649 to 1690 of SEQ ID NO: 2, deleting the intervening amino acids and replacing them with a peptidic linker, whereby the proteolytic cleavage site between Arg1648 and Glu1649, and, if present in the modified Factor VIII molecule, the proteolytic cleavage site between Arg1313 and Ala1314, is inactivated.

7. A method of treatment or prophylaxis for a bleeding disorder, comprising administering a modified Factor VIII molecule to a subject,
wherein the modified Factor VIII molecule comprises a Factor VIII molecule and a peptidic linker, wherein the Factor VIII molecule is modified by inactivating the proteolytic cleavage site between Arg1648 and Glu1649, and, if present in the Factor VIII molecule, the proteolytic cleavage site between Arg1313 and Ala1314, and
wherein the modified Factor VIII molecule is administered at a dosage of 20 IU/kg to 50 IU/kg, while maintaining or increasing the plasma stability of the Factor VIII molecule as compared to a higher dosage of an administered human wild-type Factor VIII molecule and/or an administered B-domain deleted human Factor VIII molecule in which Asn745 is fused to Pro1640.

8. The method of claim 7, wherein the modified FVIII is administered intravenously.

9. The method of claim 7, wherein the modified Factor VIII comprises SEQ ID NO: 2 modified to have a first amino acid selected from the amino acids at positions 741 to 1647 of SEQ ID NO: 2 indirectly fused to a second amino acid selected from the amino acids at positions 1649 to 1690 of SEQ ID NO: 2, deleting the intervening amino acids and replacing them with a peptidic linker, whereby the proteolytic cleavage site between Arg1648 and Glu1649, and, if present in the modified Factor VIII molecule, the proteolytic cleavage site between Arg1313 and Ala1314, is inactivated.

10. The method of claim 1, wherein the dosage of the modified Factor VIII molecule is 25% lower than the higher dosage of an administered human wild-type Factor VIII molecule and/or an administered B-domain deleted human Factor VIII molecule in which Asn745 is fused to Pro1640.

11. The method of claim 1, wherein the dosage of the modified Factor VIII molecule is 10% lower than the higher dosage of an administered human wild-type Factor VIII molecule and/or an administered B-domain deleted human Factor VIII molecule in which Asn745 is fused to Pro1640.

12. The method of claim 1, wherein the modified Factor VIII molecule is fused to an immunoglobulin Fc region.

13. The method of claim 4, wherein the dosage of the modified Factor VIII molecule is 25% lower than the higher dosage of an administered human wild-type Factor VIII molecule and/or an administered B-domain deleted human Factor VIII molecule in which Asn745 is fused to Pro1640.

14. The method of claim 4, wherein the dosage of the modified Factor VIII molecule is 10% lower than the higher dosage of an administered human wild-type Factor VIII molecule and/or an administered B-domain deleted human Factor VIII molecule in which Asn745 is fused to Pro1640.

15. The method of claim 4, wherein the modified Factor VIII molecule is fused to an immunoglobulin Fc region.

16. The method of claim 7, wherein the dosage of the modified Factor VIII molecule is 25% lower than the higher dosage of an administered human wild-type Factor VIII molecule and/or an administered B-domain deleted human Factor VIII molecule in which Asn745 is fused to Pro1640.

17. The method of claim 7, wherein the dosage of the modified Factor VIII molecule is 10% lower than the higher dosage of an administered human wild-type Factor VIII molecule and/or an administered B-domain deleted human Factor VIII molecule in which Asn745 is fused to Pro1640.

18. The method of claim 7, wherein the modified Factor VIII molecule is fused to an immunoglobulin Fc region.

* * * * *

SEQUENCE LISTING

```
<160> NUMBER OF SEQ ID NOS: 2

<210> SEQ ID NO 1
<211> LENGTH: 6996
<212> TYPE: DNA
<213> ORGANISM: homo sapiens
<220> FEATURE:
<221> NAME/KEY: CDS
<222> LOCATION: (1)..(6996)

<400> SEQUENCE: 1 gcc acc aga aga tac tac ctg ggt gca gtg gaa ctg tca tgg gac tat    48
Ala Thr Arg Arg Tyr Tyr Leu Gly Ala Val Glu Leu Ser Trp Asp Tyr
1               5                   10                  15 atg caa agt gat ctc ggt gag ctg cct gtg gac gca aga ttt cct cct    96
Met Gln Ser Asp Leu Gly Glu Leu Pro Val Asp Ala Arg Phe Pro Pro
            20                  25                  30 aga gtg cca aaa tct ttt cca ttc aac acc tca gtc gtg tac aaa aag   144
Arg Val Pro Lys Ser Phe Pro Phe Asn Thr Ser Val Val Tyr Lys Lys
        35                  40                  45 act ctg ttt gta gaa ttc acg gat cac ctt ttc aac atc gct aag cca   192
Thr Leu Phe Val Glu Phe Thr Asp His Leu Phe Asn Ile Ala Lys Pro
    50                  55                  60 agg cca ccc tgg atg ggt ctg cta ggt cct acc atc cag gct gag gtt   240
```

```
Arg Pro Pro Trp Met Gly Leu Leu Gly Pro Thr Ile Gln Ala Glu Val
 65              70                  75                  80 tat gat aca gtg gtc att aca ctt aag aac atg gct tcc cat cct gtc        288
Tyr Asp Thr Val Val Ile Thr Leu Lys Asn Met Ala Ser His Pro Val
                85                  90                  95 agt ctt cat gct gtt ggt gta tcc tac tgg aaa gct tct gag gga gct        336
Ser Leu His Ala Val Gly Val Ser Tyr Trp Lys Ala Ser Glu Gly Ala
            100                 105                 110 gaa tat gat gat cag acc agt caa agg gag aaa gaa gat gat aaa gtc        384
Glu Tyr Asp Asp Gln Thr Ser Gln Arg Glu Lys Glu Asp Asp Lys Val
                115                 120                 125 ttc cct ggt gga agc cat aca tat gtc tgg cag gtc ctg aaa gag aat        432
Phe Pro Gly Gly Ser His Thr Tyr Val Trp Gln Val Leu Lys Glu Asn
130                 135                 140 ggt cca atg gcc tct gac cca ctg tgc ctt acc tac tca tat ctt tct        480
Gly Pro Met Ala Ser Asp Pro Leu Cys Leu Thr Tyr Ser Tyr Leu Ser
145                 150                 155                 160 cat gtg gac ctg gta aaa gac ttg aat tca ggc ctc att gga gcc cta        528
His Val Asp Leu Val Lys Asp Leu Asn Ser Gly Leu Ile Gly Ala Leu
                165                 170                 175 cta gta tgt aga gaa ggg agt ctg gcc aag gaa aag aca cag acc ttg        576
Leu Val Cys Arg Glu Gly Ser Leu Ala Lys Glu Lys Thr Gln Thr Leu
                180                 185                 190 cac aaa ttt ata cta ctt ttt gct gta ttt gat gaa ggg aaa agt tgg        624
His Lys Phe Ile Leu Leu Phe Ala Val Phe Asp Glu Gly Lys Ser Trp
            195                 200                 205 cac tca gaa aca aag aac tcc ttg atg cag gat agg gat gct gca tct        672
His Ser Glu Thr Lys Asn Ser Leu Met Gln Asp Arg Asp Ala Ala Ser
            210                 215                 220 gct cgg gcc tgg cct aaa atg cac aca gtc aat ggt tat gta aac agg        720
Ala Arg Ala Trp Pro Lys Met His Thr Val Asn Gly Tyr Val Asn Arg
225                 230                 235                 240 tct ctg cca ggt ctg att gga tgc cac agg aaa tca gtc tat tgg cat        768
Ser Leu Pro Gly Leu Ile Gly Cys His Arg Lys Ser Val Tyr Trp His
                245                 250                 255 gtg att gga atg ggc acc act cct gaa gtg cac tca ata ttc ctc gaa        816
Val Ile Gly Met Gly Thr Thr Pro Glu Val His Ser Ile Phe Leu Glu
                260                 265                 270 ggt cac aca ttt ctt gtg agg aac cat cgc cag gcg tcc ttg gaa atc        864
Gly His Thr Phe Leu Val Arg Asn His Arg Gln Ala Ser Leu Glu Ile
            275                 280                 285 tcg cca ata act ttc ctt act gct caa aca ctc ttg atg gac ctt gga        912
Ser Pro Ile Thr Phe Leu Thr Ala Gln Thr Leu Leu Met Asp Leu Gly
            290                 295                 300 cag ttt cta ctg ttt tgt cat atc tct tcc cac caa cat gat ggc atg        960
Gln Phe Leu Leu Phe Cys His Ile Ser Ser His Gln His Asp Gly Met
305                 310                 315                 320 gaa gct tat gtc aaa gta gac agc tgt cca gag gaa ccc caa cta cga       1008
Glu Ala Tyr Val Lys Val Asp Ser Cys Pro Glu Glu Pro Gln Leu Arg
                325                 330                 335 atg aaa aat aat gaa gaa gcg gaa gac tat gat gat gat ctt act gat       1056
Met Lys Asn Asn Glu Glu Ala Glu Asp Tyr Asp Asp Asp Leu Thr Asp
                340                 345                 350 tct gaa atg gat gtg gtc agg ttt gat gat gac aac tct cct tcc ttt       1104
Ser Glu Met Asp Val Val Arg Phe Asp Asp Asp Asn Ser Pro Ser Phe
            355                 360                 365 atc caa att cgc tca gtt gcc aag aag cat cct aaa act tgg gta cat       1152
Ile Gln Ile Arg Ser Val Ala Lys Lys His Pro Lys Thr Trp Val His
            370                 375                 380
```

| | | |
|---|---|---|
| tac att gct gct gaa gag gag gac tgg gac tat gct ccc tta gtc ctc<br>Tyr Ile Ala Ala Glu Glu Glu Asp Trp Asp Tyr Ala Pro Leu Val Leu<br>385                           390                     395               400 | 1200 |
| gcc ccc gat gac aga agt tat aaa agt caa tat ttg aac aat ggc cct<br>Ala Pro Asp Asp Arg Ser Tyr Lys Ser Gln Tyr Leu Asn Asn Gly Pro<br>                    405                     410                     415 | 1248 |
| cag cgg att ggt agg aag tac aaa aaa gtc cga ttt atg gca tac aca<br>Gln Arg Ile Gly Arg Lys Tyr Lys Lys Val Arg Phe Met Ala Tyr Thr<br>               420                     425                   430 | 1296 |
| gat gaa acc ttt aag act cgt gaa gct att cag cat gaa tca gga atc<br>Asp Glu Thr Phe Lys Thr Arg Glu Ala Ile Gln His Glu Ser Gly Ile<br>           435                    440                   445 | 1344 |
| ttg gga cct tta ctt tat ggg gaa gtt gga gac aca ctg ttg att ata<br>Leu Gly Pro Leu Leu Tyr Gly Glu Val Gly Asp Thr Leu Leu Ile Ile<br>450                           455                     460 | 1392 |
| ttt aag aat caa gca agc aga cca tat aac atc tac cct cac gga atc<br>Phe Lys Asn Gln Ala Ser Arg Pro Tyr Asn Ile Tyr Pro His Gly Ile<br>465                         470                     475               480 | 1440 |
| act gat gtc cgt cct ttg tat tca agg aga tta cca aaa ggt gta aaa<br>Thr Asp Val Arg Pro Leu Tyr Ser Arg Arg Leu Pro Lys Gly Val Lys<br>                    485                     490                    495 | 1488 |
| cat ttg aag gat ttt cca att ctg cca gga gaa ata ttc aaa tat aaa<br>His Leu Lys Asp Phe Pro Ile Leu Pro Gly Glu Ile Phe Lys Tyr Lys<br>               500                     505                   510 | 1536 |
| tgg aca gtg act gta gaa gat ggg cca act aaa tca gat cct cgg tgc<br>Trp Thr Val Thr Val Glu Asp Gly Pro Thr Lys Ser Asp Pro Arg Cys<br>          515                    520                   525 | 1584 |
| ctg acc cgc tat tac tct agt ttc gtt aat atg gag aga gat cta gct<br>Leu Thr Arg Tyr Tyr Ser Ser Phe Val Asn Met Glu Arg Asp Leu Ala<br>530                           535                     540 | 1632 |
| tca gga ctc att ggc cct ctc ctc atc tgc tac aaa gaa tct gta gat<br>Ser Gly Leu Ile Gly Pro Leu Leu Ile Cys Tyr Lys Glu Ser Val Asp<br>545                         550                     555               560 | 1680 |
| caa aga gga aac cag ata atg tca gac aag agg aat gtc atc ctg ttt<br>Gln Arg Gly Asn Gln Ile Met Ser Asp Lys Arg Asn Val Ile Leu Phe<br>               565                     570                   575 | 1728 |
| tct gta ttt gat gag aac cga agc tgg tac ctc aca gag aat ata caa<br>Ser Val Phe Asp Glu Asn Arg Ser Trp Tyr Leu Thr Glu Asn Ile Gln<br>                    580                     585                   590 | 1776 |
| cgc ttt ctc ccc aat cca gct gga gtg cag ctt gag gat cca gag ttc<br>Arg Phe Leu Pro Asn Pro Ala Gly Val Gln Leu Glu Asp Pro Glu Phe<br>          595                    600                   605 | 1824 |
| caa gcc tcc aac atc atg cac agc atc aat ggc tat gtt ttt gat agt<br>Gln Ala Ser Asn Ile Met His Ser Ile Asn Gly Tyr Val Phe Asp Ser<br>610                           615                     620 | 1872 |
| ttg cag ttg tca gtt tgt ttg cat gag gtg gca tac tgg tac att cta<br>Leu Gln Leu Ser Val Cys Leu His Glu Val Ala Tyr Trp Tyr Ile Leu<br>625                           630                     635               640 | 1920 |
| agc att gga gca cag act gac ttc ctt tct gtc ttc ttc tct gga tat<br>Ser Ile Gly Ala Gln Thr Asp Phe Leu Ser Val Phe Phe Ser Gly Tyr<br>               645                     650                   655 | 1968 |
| acc ttc aaa cac aaa atg gtc tat gaa gac aca ctc acc cta ttc cca<br>Thr Phe Lys His Lys Met Val Tyr Glu Asp Thr Leu Thr Leu Phe Pro<br>               660                     665                   670 | 2016 |
| ttc tca gga gaa act gtc ttc atg tcg atg gaa aac cca ggt cta tgg<br>Phe Ser Gly Glu Thr Val Phe Met Ser Met Glu Asn Pro Gly Leu Trp<br>          675                    680                   685 | 2064 |
| att ctg ggg tgc cac aac tca gac ttt cgg aac aga ggc atg acc gcc<br>Ile Leu Gly Cys His Asn Ser Asp Phe Arg Asn Arg Gly Met Thr Ala<br>690                           695                     700 | 2112 |

```
tta ctg aag gtt tct agt tgt gac aag aac act ggt gat tat tac gag    2160
Leu Leu Lys Val Ser Ser Cys Asp Lys Asn Thr Gly Asp Tyr Tyr Glu
705             710                 715                 720 gac agt tat gaa gat att tca gca tac ttg ctg agt aaa aac aat gcc    2208
Asp Ser Tyr Glu Asp Ile Ser Ala Tyr Leu Leu Ser Lys Asn Asn Ala
                725                 730                 735 att gaa cca aga agc ttc tcc cag aat tca aga cac cgt agc act agg    2256
Ile Glu Pro Arg Ser Phe Ser Gln Asn Ser Arg His Arg Ser Thr Arg
            740                 745                 750 caa aag caa ttt aat gcc acc aca att cca gaa aat gac ata gag aag    2304
Gln Lys Gln Phe Asn Ala Thr Thr Ile Pro Glu Asn Asp Ile Glu Lys
        755                 760                 765 act gac cct tgg ttt gca cac aga aca cct atg cct aaa ata caa aat    2352
Thr Asp Pro Trp Phe Ala His Arg Thr Pro Met Pro Lys Ile Gln Asn
770                 775                 780 gtc tcc tct agt gat ttg ttg atg ctc ttg cga cag agt cct act cca    2400
Val Ser Ser Ser Asp Leu Leu Met Leu Leu Arg Gln Ser Pro Thr Pro
785                 790                 795                 800 cat ggg cta tcc tta tct gat ctc caa gaa gcc aaa tat gag act ttt    2448
His Gly Leu Ser Leu Ser Asp Leu Gln Glu Ala Lys Tyr Glu Thr Phe
                805                 810                 815 tct gat gat cca tca cct gga gca ata gac agt aat aac agc ctg tct    2496
Ser Asp Asp Pro Ser Pro Gly Ala Ile Asp Ser Asn Asn Ser Leu Ser
            820                 825                 830 gaa atg aca cac ttc agg cca cag ctc cat cac agt ggg gac atg gta    2544
Glu Met Thr His Phe Arg Pro Gln Leu His His Ser Gly Asp Met Val
        835                 840                 845 ttt acc cct gag tca ggc ctc caa tta aga tta aat gag aaa ctg ggg    2592
Phe Thr Pro Glu Ser Gly Leu Gln Leu Arg Leu Asn Glu Lys Leu Gly
850                 855                 860 aca act gca gca aca gag ttg aag aaa ctt gat ttc aaa gtt tct agt    2640
Thr Thr Ala Ala Thr Glu Leu Lys Lys Leu Asp Phe Lys Val Ser Ser
865                 870                 875                 880 aca tca aat aat ctg att tca aca att cca tca gac aat ttg gca gca    2688
Thr Ser Asn Asn Leu Ile Ser Thr Ile Pro Ser Asp Asn Leu Ala Ala
                885                 890                 895 ggt act gat aat aca agt tcc tta gga ccc cca agt atg cca gtt cat    2736
Gly Thr Asp Asn Thr Ser Ser Leu Gly Pro Pro Ser Met Pro Val His
            900                 905                 910 tat gat agt caa tta gat acc act cta ttt ggc aaa aag tca tct ccc    2784
Tyr Asp Ser Gln Leu Asp Thr Thr Leu Phe Gly Lys Lys Ser Ser Pro
        915                 920                 925 ctt act gag tct ggt gga cct ctg agc ttg agt gaa gaa aat aat gat    2832
Leu Thr Glu Ser Gly Gly Pro Leu Ser Leu Ser Glu Glu Asn Asn Asp
930                 935                 940 tca aag ttg tta gaa tca ggt tta atg aat agc caa gaa agt tca tgg    2880
Ser Lys Leu Leu Glu Ser Gly Leu Met Asn Ser Gln Glu Ser Ser Trp
945                 950                 955                 960 gga aaa aat gta tcg tca aca gag agt ggt agg tta ttt aaa ggg aaa    2928
Gly Lys Asn Val Ser Ser Thr Glu Ser Gly Arg Leu Phe Lys Gly Lys
                965                 970                 975 aga gct cat gga cct gct ttg ttg act aaa gat aat gcc tta ttc aaa    2976
Arg Ala His Gly Pro Ala Leu Leu Thr Lys Asp Asn Ala Leu Phe Lys
            980                 985                 990 gtt agc atc tct ttg tta aag aca aac aaa act tcc aat aat tca gca    3024
Val Ser Ile Ser Leu Leu Lys Thr Asn Lys Thr Ser Asn Asn Ser Ala
        995                 1000                1005 act aat aga aag act cac att gat ggc cca tca tta tta att gag       3069
Thr Asn Arg Lys Thr His Ile Asp Gly Pro Ser Leu Leu Ile Glu
```

|       |     |     |     |     |     |     |     |     |     |     |     |     |     |     |      |
|-------|-----|-----|-----|-----|-----|-----|-----|-----|-----|-----|-----|-----|-----|-----|------|
|       |     |1010 |     |     |     |1015 |     |     |     |1020 |     |     |     |     |      |
| aat   | agt | cca | tca | gtc | tgg | caa | aat | ata | tta | gaa | agt | gac | act | gag | 3114 |
| Asn   | Ser | Pro | Ser | Val | Trp | Gln | Asn | Ile | Leu | Glu | Ser | Asp | Thr | Glu |      |
|       |1025 |     |     |     |1030 |     |     |     |1035 |     |     |     |     |     |      |
| ttt   | aaa | aaa | gtg | aca | cct | ttg | att | cat | gac | aga | atg | ctt | atg | gac | 3159 |
| Phe   | Lys | Lys | Val | Thr | Pro | Leu | Ile | His | Asp | Arg | Met | Leu | Met | Asp |      |
|       |1040 |     |     |     |1045 |     |     |     |1050 |     |     |     |     |     |      |
| aaa   | aat | gct | aca | gct | ttg | agg | cta | aat | cat | atg | tca | aat | aaa | act | 3204 |
| Lys   | Asn | Ala | Thr | Ala | Leu | Arg | Leu | Asn | His | Met | Ser | Asn | Lys | Thr |      |
|       |1055 |     |     |     |1060 |     |     |     |1065 |     |     |     |     |     |      |
| act   | tca | tca | aaa | aac | atg | gaa | atg | gtc | caa | cag | aaa | aaa | gag | ggc | 3249 |
| Thr   | Ser | Ser | Lys | Asn | Met | Glu | Met | Val | Gln | Gln | Lys | Lys | Glu | Gly |      |
|       |1070 |     |     |     |1075 |     |     |     |1080 |     |     |     |     |     |      |
| ccc   | att | cca | cca | gat | gca | caa | aat | cca | gat | atg | tcg | ttc | ttt | aag | 3294 |
| Pro   | Ile | Pro | Pro | Asp | Ala | Gln | Asn | Pro | Asp | Met | Ser | Phe | Phe | Lys |      |
|       |1085 |     |     |     |1090 |     |     |     |1095 |     |     |     |     |     |      |
| atg   | cta | ttc | ttg | cca | gaa | tca | gca | agg | tgg | ata | caa | agg | act | cat | 3339 |
| Met   | Leu | Phe | Leu | Pro | Glu | Ser | Ala | Arg | Trp | Ile | Gln | Arg | Thr | His |      |
|       |1100 |     |     |     |1105 |     |     |     |1110 |     |     |     |     |     |      |
| gga   | aag | aac | tct | ctg | aac | tct | ggg | caa | ggc | ccc | agt | cca | aag | caa | 3384 |
| Gly   | Lys | Asn | Ser | Leu | Asn | Ser | Gly | Gln | Gly | Pro | Ser | Pro | Lys | Gln |      |
|       |1115 |     |     |     |1120 |     |     |     |1125 |     |     |     |     |     |      |
| tta   | gta | tcc | tta | gga | cca | gaa | aaa | tct | gtg | gaa | ggt | cag | aat | ttc | 3429 |
| Leu   | Val | Ser | Leu | Gly | Pro | Glu | Lys | Ser | Val | Glu | Gly | Gln | Asn | Phe |      |
|       |1130 |     |     |     |1135 |     |     |     |1140 |     |     |     |     |     |      |
| ttg   | tct | gag | aaa | aac | aaa | gtg | gta | gta | gga | aag | ggt | gaa | ttt | aca | 3474 |
| Leu   | Ser | Glu | Lys | Asn | Lys | Val | Val | Val | Gly | Lys | Gly | Glu | Phe | Thr |      |
|       |1145 |     |     |     |1150 |     |     |     |1155 |     |     |     |     |     |      |
| aag   | gac | gta | gga | ctc | aaa | gag | atg | gtt | ttt | cca | agc | agc | aga | aac | 3519 |
| Lys   | Asp | Val | Gly | Leu | Lys | Glu | Met | Val | Phe | Pro | Ser | Ser | Arg | Asn |      |
|       |1160 |     |     |     |1165 |     |     |     |1170 |     |     |     |     |     |      |
| cta   | ttt | ctt | act | aac | ttg | gat | aat | tta | cat | gaa | aat | aat | aca | cac | 3564 |
| Leu   | Phe | Leu | Thr | Asn | Leu | Asp | Asn | Leu | His | Glu | Asn | Asn | Thr | His |      |
|       |1175 |     |     |     |1180 |     |     |     |1185 |     |     |     |     |     |      |
| aat   | caa | gaa | aaa | aaa | att | cag | gaa | gaa | ata | gaa | aag | aag | gaa | aca | 3609 |
| Asn   | Gln | Glu | Lys | Lys | Ile | Gln | Glu | Glu | Ile | Glu | Lys | Lys | Glu | Thr |      |
|       |1190 |     |     |     |1195 |     |     |     |1200 |     |     |     |     |     |      |
| tta   | atc | caa | gag | aat | gta | gtt | ttg | cct | cag | ata | cat | aca | gtg | act | 3654 |
| Leu   | Ile | Gln | Glu | Asn | Val | Val | Leu | Pro | Gln | Ile | His | Thr | Val | Thr |      |
|       |1205 |     |     |     |1210 |     |     |     |1215 |     |     |     |     |     |      |
| ggc   | act | aag | aat | ttc | atg | aag | aac | ctt | ttc | tta | ctg | agc | act | agg | 3699 |
| Gly   | Thr | Lys | Asn | Phe | Met | Lys | Asn | Leu | Phe | Leu | Leu | Ser | Thr | Arg |      |
|       |1220 |     |     |     |1225 |     |     |     |1230 |     |     |     |     |     |      |
| caa   | aat | gta | gaa | ggt | tca | tat | gac | ggg | gca | tat | gct | cca | gta | ctt | 3744 |
| Gln   | Asn | Val | Glu | Gly | Ser | Tyr | Asp | Gly | Ala | Tyr | Ala | Pro | Val | Leu |      |
|       |1235 |     |     |     |1240 |     |     |     |1245 |     |     |     |     |     |      |
| caa   | gat | ttt | agg | tca | tta | aat | gat | tca | aca | aat | aga | aca | aag | aaa | 3789 |
| Gln   | Asp | Phe | Arg | Ser | Leu | Asn | Asp | Ser | Thr | Asn | Arg | Thr | Lys | Lys |      |
|       |1250 |     |     |     |1255 |     |     |     |1260 |     |     |     |     |     |      |
| cac   | aca | gct | cat | ttc | tca | aaa | aaa | ggg | gag | gaa | gaa | aac | ttg | gaa | 3834 |
| His   | Thr | Ala | His | Phe | Ser | Lys | Lys | Gly | Glu | Glu | Glu | Asn | Leu | Glu |      |
|       |1265 |     |     |     |1270 |     |     |     |1275 |     |     |     |     |     |      |
| ggc   | ttg | gga | aat | caa | acc | aag | caa | att | gta | gag | aaa | tat | gca | tgc | 3879 |
| Gly   | Leu | Gly | Asn | Gln | Thr | Lys | Gln | Ile | Val | Glu | Lys | Tyr | Ala | Cys |      |
|       |1280 |     |     |     |1285 |     |     |     |1290 |     |     |     |     |     |      |
| acc   | aca | agg | ata | tct | cct | aat | aca | agc | cag | cag | aat | ttt | gtc | acg | 3924 |
| Thr   | Thr | Arg | Ile | Ser | Pro | Asn | Thr | Ser | Gln | Gln | Asn | Phe | Val | Thr |      |
|       |1295 |     |     |     |1300 |     |     |     |1305 |     |     |     |     |     |      |
| caa   | cgt | agt | aag | aga | gct | ttg | aaa | caa | ttc | aga | ctc | cca | cta | gaa | 3969 |

```
               Gln Arg Ser Lys Arg Ala Leu Lys Gln Phe Arg Leu Pro Leu Glu
                   1310                1315                1320 gaa aca gaa ctt gaa aaa agg ata att gtg gat gac acc tca acc              4014
Glu Thr Glu Leu Glu Lys Arg Ile Ile Val Asp Asp Thr Ser Thr
    1325                1330                1335 cag tgg tcc aaa aac atg aaa cat ttg acc ccg agc acc ctc aca              4059
Gln Trp Ser Lys Asn Met Lys His Leu Thr Pro Ser Thr Leu Thr
    1340                1345                1350 cag ata gac tac aat gag aag gag aaa ggg gcc att act cag tct              4104
Gln Ile Asp Tyr Asn Glu Lys Glu Lys Gly Ala Ile Thr Gln Ser
    1355                1360                1365 ccc tta tca gat tgc ctt acg agg agt cat agc atc cct caa gca              4149
Pro Leu Ser Asp Cys Leu Thr Arg Ser His Ser Ile Pro Gln Ala
    1370                1375                1380 aat aga tct cca tta ccc att gca aag gta tca tca ttt cca tct              4194
Asn Arg Ser Pro Leu Pro Ile Ala Lys Val Ser Ser Phe Pro Ser
    1385                1390                1395 att aga cct ata tat ctg acc agg gtc cta ttc caa gac aac tct              4239
Ile Arg Pro Ile Tyr Leu Thr Arg Val Leu Phe Gln Asp Asn Ser
    1400                1405                1410 tct cat ctt cca gca gca tct tat aga aag aaa gat tct ggg gtc              4284
Ser His Leu Pro Ala Ala Ser Tyr Arg Lys Lys Asp Ser Gly Val
    1415                1420                1425 caa gaa agc agt cat ttc tta caa gga gcc aaa aaa aat aac ctt              4329
Gln Glu Ser Ser His Phe Leu Gln Gly Ala Lys Lys Asn Asn Leu
    1430                1435                1440 tct tta gcc att cta acc ttg gag atg act ggt gat caa aga gag              4374
Ser Leu Ala Ile Leu Thr Leu Glu Met Thr Gly Asp Gln Arg Glu
    1445                1450                1455 gtt ggc tcc ctg ggg aca agt gcc aca aat tca gtc aca tac aag              4419
Val Gly Ser Leu Gly Thr Ser Ala Thr Asn Ser Val Thr Tyr Lys
    1460                1465                1470 aaa gtt gag aac act gtt ctc ccg aaa cca gac ttg ccc aaa aca              4464
Lys Val Glu Asn Thr Val Leu Pro Lys Pro Asp Leu Pro Lys Thr
    1475                1480                1485 tct ggc aaa gtt gaa ttg ctt cca aaa gtt cac att tat cag aag              4509
Ser Gly Lys Val Glu Leu Leu Pro Lys Val His Ile Tyr Gln Lys
    1490                1495                1500 gac cta ttc cct acg gaa act agc aat ggg tct cct ggc cat ctg              4554
Asp Leu Phe Pro Thr Glu Thr Ser Asn Gly Ser Pro Gly His Leu
    1505                1510                1515 gat ctc gtg gaa ggg agc ctt ctt cag gga aca gag gga gcg att              4599
Asp Leu Val Glu Gly Ser Leu Leu Gln Gly Thr Glu Gly Ala Ile
    1520                1525                1530 aag tgg aat gaa gca aac aga cct gga aaa gtt ccc ttt ctg aga              4644
Lys Trp Asn Glu Ala Asn Arg Pro Gly Lys Val Pro Phe Leu Arg
    1535                1540                1545 gta gca aca gaa agc tct gca aag act ccc tcc aag cta ttg gat              4689
Val Ala Thr Glu Ser Ser Ala Lys Thr Pro Ser Lys Leu Leu Asp
    1550                1555                1560 cct ctt gct tgg gat aac cac tat ggt act cag ata cca aaa gaa              4734
Pro Leu Ala Trp Asp Asn His Tyr Gly Thr Gln Ile Pro Lys Glu
    1565                1570                1575 gag tgg aaa tcc caa gag aag tca cca gaa aaa aca gct ttt aag              4779
Glu Trp Lys Ser Gln Glu Lys Ser Pro Glu Lys Thr Ala Phe Lys
    1580                1585                1590 aaa aag gat acc att ttg tcc ctg aac gct tgt gaa agc aat cat              4824
Lys Lys Asp Thr Ile Leu Ser Leu Asn Ala Cys Glu Ser Asn His
    1595                1600                1605
```

|  |  |  |  |  |  |  |  |  |  |  |  |  |  |  |
|---|---|---|---|---|---|---|---|---|---|---|---|---|---|---|
| gca | ata | gca | gca | ata | aat | gag | gga | caa | aat | aag | ccc | gaa | ata | gaa | 4869 |
| Ala | Ile | Ala | Ala | Ile | Asn | Glu | Gly | Gln | Asn | Lys | Pro | Glu | Ile | Glu |  |
|  | 1610 |  |  |  | 1615 |  |  |  |  | 1620 |  |  |  |  |  |
| gtc | acc | tgg | gca | aag | caa | ggt | agg | act | gaa | agg | ctg | tgc | tct | caa | 4914 |
| Val | Thr | Trp | Ala | Lys | Gln | Gly | Arg | Thr | Glu | Arg | Leu | Cys | Ser | Gln |  |
|  | 1625 |  |  |  | 1630 |  |  |  |  | 1635 |  |  |  |  |  |
| aac | cca | cca | gtc | ttg | aaa | cgc | cat | caa | cgg | gaa | ata | act | cgt | act | 4959 |
| Asn | Pro | Pro | Val | Leu | Lys | Arg | His | Gln | Arg | Glu | Ile | Thr | Arg | Thr |  |
| 1640 |  |  |  |  | 1645 |  |  |  |  | 1650 |  |  |  |  |  |
| act | ctt | cag | tca | gat | caa | gag | gaa | att | gac | tat | gat | gat | acc | ata | 5004 |
| Thr | Leu | Gln | Ser | Asp | Gln | Glu | Glu | Ile | Asp | Tyr | Asp | Asp | Thr | Ile |  |
| 1655 |  |  |  |  | 1660 |  |  |  |  | 1665 |  |  |  |  |  |
| tca | gtt | gaa | atg | aag | aag | gaa | gat | ttt | gac | att | tat | gat | gag | gat | 5049 |
| Ser | Val | Glu | Met | Lys | Lys | Glu | Asp | Phe | Asp | Ile | Tyr | Asp | Glu | Asp |  |
| 1670 |  |  |  |  | 1675 |  |  |  |  | 1680 |  |  |  |  |  |
| gaa | aat | cag | agc | ccc | cgc | agc | ttt | caa | aag | aaa | aca | cga | cac | tat | 5094 |
| Glu | Asn | Gln | Ser | Pro | Arg | Ser | Phe | Gln | Lys | Lys | Thr | Arg | His | Tyr |  |
| 1685 |  |  |  |  | 1690 |  |  |  |  | 1695 |  |  |  |  |  |
| ttt | att | gct | gca | gtg | gag | agg | ctc | tgg | gat | tat | ggg | atg | agt | agc | 5139 |
| Phe | Ile | Ala | Ala | Val | Glu | Arg | Leu | Trp | Asp | Tyr | Gly | Met | Ser | Ser |  |
| 1700 |  |  |  |  | 1705 |  |  |  |  | 1710 |  |  |  |  |  |
| tcc | cca | cat | gtt | cta | aga | aac | agg | gct | cag | agt | ggc | agt | gtc | cct | 5184 |
| Ser | Pro | His | Val | Leu | Arg | Asn | Arg | Ala | Gln | Ser | Gly | Ser | Val | Pro |  |
| 1715 |  |  |  |  | 1720 |  |  |  |  | 1725 |  |  |  |  |  |
| cag | ttc | aag | aaa | gtt | gtt | ttc | cag | gaa | ttt | act | gat | ggc | tcc | ttt | 5229 |
| Gln | Phe | Lys | Lys | Val | Val | Phe | Gln | Glu | Phe | Thr | Asp | Gly | Ser | Phe |  |
| 1730 |  |  |  |  | 1735 |  |  |  |  | 1740 |  |  |  |  |  |
| act | cag | ccc | tta | tac | cgt | gga | gaa | cta | aat | gaa | cat | ttg | gga | ctc | 5274 |
| Thr | Gln | Pro | Leu | Tyr | Arg | Gly | Glu | Leu | Asn | Glu | His | Leu | Gly | Leu |  |
| 1745 |  |  |  |  | 1750 |  |  |  |  | 1755 |  |  |  |  |  |
| ctg | ggg | cca | tat | ata | aga | gca | gaa | gtt | gaa | gat | aat | atc | atg | gta | 5319 |
| Leu | Gly | Pro | Tyr | Ile | Arg | Ala | Glu | Val | Glu | Asp | Asn | Ile | Met | Val |  |
| 1760 |  |  |  |  | 1765 |  |  |  |  | 1770 |  |  |  |  |  |
| act | ttc | aga | aat | cag | gcc | tct | cgt | ccc | tat | tcc | ttc | tat | tct | agc | 5364 |
| Thr | Phe | Arg | Asn | Gln | Ala | Ser | Arg | Pro | Tyr | Ser | Phe | Tyr | Ser | Ser |  |
| 1775 |  |  |  |  | 1780 |  |  |  |  | 1785 |  |  |  |  |  |
| ctt | att | tct | tat | gag | gaa | gat | cag | agg | caa | gga | gca | gaa | cct | aga | 5409 |
| Leu | Ile | Ser | Tyr | Glu | Glu | Asp | Gln | Arg | Gln | Gly | Ala | Glu | Pro | Arg |  |
| 1790 |  |  |  |  | 1795 |  |  |  |  | 1800 |  |  |  |  |  |
| aaa | aac | ttt | gtc | aag | cct | aat | gaa | acc | aaa | act | tac | ttt | tgg | aaa | 5454 |
| Lys | Asn | Phe | Val | Lys | Pro | Asn | Glu | Thr | Lys | Thr | Tyr | Phe | Trp | Lys |  |
| 1805 |  |  |  |  | 1810 |  |  |  |  | 1815 |  |  |  |  |  |
| gtg | caa | cat | cat | atg | gca | ccc | act | aaa | gat | gag | ttt | gac | tgc | aaa | 5499 |
| Val | Gln | His | His | Met | Ala | Pro | Thr | Lys | Asp | Glu | Phe | Asp | Cys | Lys |  |
| 1820 |  |  |  |  | 1825 |  |  |  |  | 1830 |  |  |  |  |  |
| gcc | tgg | gct | tat | ttc | tct | gat | gtt | gac | ctg | gaa | aaa | gat | gtg | cac | 5544 |
| Ala | Trp | Ala | Tyr | Phe | Ser | Asp | Val | Asp | Leu | Glu | Lys | Asp | Val | His |  |
| 1835 |  |  |  |  | 1840 |  |  |  |  | 1845 |  |  |  |  |  |
| tca | ggc | ctg | att | gga | ccc | ctt | ctg | gtc | tgc | cac | act | aac | aca | ctg | 5589 |
| Ser | Gly | Leu | Ile | Gly | Pro | Leu | Leu | Val | Cys | His | Thr | Asn | Thr | Leu |  |
| 1850 |  |  |  |  | 1855 |  |  |  |  | 1860 |  |  |  |  |  |
| aac | cct | gct | cat | ggg | aga | caa | gtg | aca | gta | cag | gaa | ttt | gct | ctg | 5634 |
| Asn | Pro | Ala | His | Gly | Arg | Gln | Val | Thr | Val | Gln | Glu | Phe | Ala | Leu |  |
| 1865 |  |  |  |  | 1870 |  |  |  |  | 1875 |  |  |  |  |  |
| ttt | ttc | acc | atc | ttt | gat | gag | acc | aaa | agc | tgg | tac | ttc | act | gaa | 5679 |
| Phe | Phe | Thr | Ile | Phe | Asp | Glu | Thr | Lys | Ser | Trp | Tyr | Phe | Thr | Glu |  |
| 1880 |  |  |  |  | 1885 |  |  |  |  | 1890 |  |  |  |  |  |
| aat | atg | gaa | aga | aac | tgc | agg | gct | ccc | tgc | aat | atc | cag | atg | gaa | 5724 |
| Asn | Met | Glu | Arg | Asn | Cys | Arg | Ala | Pro | Cys | Asn | Ile | Gln | Met | Glu |  |
| 1895 |  |  |  |  | 1900 |  |  |  |  | 1905 |  |  |  |  |  |

-continued

| | | | | | | | | | | | |
|---|---|---|---|---|---|---|---|---|---|---|---|
| gat | ccc | act | ttt | aaa | gag | aat | tat | cgc | ttc | cat | gca | atc | aat | ggc | 5769 |
| Asp | Pro | Thr | Phe | Lys | Glu | Asn | Tyr | Arg | Phe | His | Ala | Ile | Asn | Gly | |
| | 1910 | | | | 1915 | | | | | 1920 | | | | | |
| tac | ata | atg | gat | aca | cta | cct | ggc | tta | gta | atg | gct | cag | gat | caa | 5814 |
| Tyr | Ile | Met | Asp | Thr | Leu | Pro | Gly | Leu | Val | Met | Ala | Gln | Asp | Gln | |
| | 1925 | | | | 1930 | | | | | 1935 | | | | | |
| agg | att | cga | tgg | tat | ctg | ctc | agc | atg | ggc | agc | aat | gaa | aac | atc | 5859 |
| Arg | Ile | Arg | Trp | Tyr | Leu | Leu | Ser | Met | Gly | Ser | Asn | Glu | Asn | Ile | |
| | 1940 | | | | 1945 | | | | | 1950 | | | | | |
| cat | tct | att | cat | ttc | agt | gga | cat | gtg | ttc | act | gta | cga | aaa | aaa | 5904 |
| His | Ser | Ile | His | Phe | Ser | Gly | His | Val | Phe | Thr | Val | Arg | Lys | Lys | |
| | 1955 | | | | 1960 | | | | | 1965 | | | | | |
| gag | gag | tat | aaa | atg | gca | ctg | tac | aat | ctc | tat | cca | ggt | gtt | ttt | 5949 |
| Glu | Glu | Tyr | Lys | Met | Ala | Leu | Tyr | Asn | Leu | Tyr | Pro | Gly | Val | Phe | |
| | 1970 | | | | 1975 | | | | | 1980 | | | | | |
| gag | aca | gtg | gaa | atg | tta | cca | tcc | aaa | gct | gga | att | tgg | cgg | gtg | 5994 |
| Glu | Thr | Val | Glu | Met | Leu | Pro | Ser | Lys | Ala | Gly | Ile | Trp | Arg | Val | |
| | 1985 | | | | 1990 | | | | | 1995 | | | | | |
| gaa | tgc | ctt | att | ggc | gag | cat | cta | cat | gct | ggg | atg | agc | aca | ctt | 6039 |
| Glu | Cys | Leu | Ile | Gly | Glu | His | Leu | His | Ala | Gly | Met | Ser | Thr | Leu | |
| | 2000 | | | | 2005 | | | | | 2010 | | | | | |
| ttt | ctg | gtg | tac | agc | aat | aag | tgt | cag | act | ccc | ctg | gga | atg | gct | 6084 |
| Phe | Leu | Val | Tyr | Ser | Asn | Lys | Cys | Gln | Thr | Pro | Leu | Gly | Met | Ala | |
| | 2015 | | | | 2020 | | | | | 2025 | | | | | |
| tct | gga | cac | att | aga | gat | ttt | cag | att | aca | gct | tca | gga | caa | tat | 6129 |
| Ser | Gly | His | Ile | Arg | Asp | Phe | Gln | Ile | Thr | Ala | Ser | Gly | Gln | Tyr | |
| | 2030 | | | | 2035 | | | | | 2040 | | | | | |
| gga | cag | tgg | gcc | cca | aag | ctg | gcc | aga | ctt | cat | tat | tcc | gga | tca | 6174 |
| Gly | Gln | Trp | Ala | Pro | Lys | Leu | Ala | Arg | Leu | His | Tyr | Ser | Gly | Ser | |
| | 2045 | | | | 2050 | | | | | 2055 | | | | | |
| atc | aat | gcc | tgg | agc | acc | aag | gag | ccc | ttt | tct | tgg | atc | aag | gtg | 6219 |
| Ile | Asn | Ala | Trp | Ser | Thr | Lys | Glu | Pro | Phe | Ser | Trp | Ile | Lys | Val | |
| | 2060 | | | | 2065 | | | | | 2070 | | | | | |
| gat | ctg | ttg | gca | cca | atg | att | att | cac | ggc | atc | aag | acc | cag | ggt | 6264 |
| Asp | Leu | Leu | Ala | Pro | Met | Ile | Ile | His | Gly | Ile | Lys | Thr | Gln | Gly | |
| | 2075 | | | | 2080 | | | | | 2085 | | | | | |
| gcc | cgt | cag | aag | ttc | tcc | agc | ctc | tac | atc | tct | cag | ttt | atc | atc | 6309 |
| Ala | Arg | Gln | Lys | Phe | Ser | Ser | Leu | Tyr | Ile | Ser | Gln | Phe | Ile | Ile | |
| | 2090 | | | | 2095 | | | | | 2100 | | | | | |
| atg | tat | agt | ctt | gat | ggg | aag | aag | tgg | cag | act | tat | cga | gga | aat | 6354 |
| Met | Tyr | Ser | Leu | Asp | Gly | Lys | Lys | Trp | Gln | Thr | Tyr | Arg | Gly | Asn | |
| | 2105 | | | | 2110 | | | | | 2115 | | | | | |
| tcc | act | gga | acc | tta | atg | gtc | ttc | ttt | ggc | aat | gtg | gat | tca | tct | 6399 |
| Ser | Thr | Gly | Thr | Leu | Met | Val | Phe | Phe | Gly | Asn | Val | Asp | Ser | Ser | |
| | 2120 | | | | 2125 | | | | | 2130 | | | | | |
| ggg | ata | aaa | cac | aat | att | ttt | aac | cct | cca | att | att | gct | cga | tac | 6444 |
| Gly | Ile | Lys | His | Asn | Ile | Phe | Asn | Pro | Pro | Ile | Ile | Ala | Arg | Tyr | |
| | 2135 | | | | 2140 | | | | | 2145 | | | | | |
| atc | cgt | ttg | cac | cca | act | cat | tat | agc | att | cgc | agc | act | ctt | cgc | 6489 |
| Ile | Arg | Leu | His | Pro | Thr | His | Tyr | Ser | Ile | Arg | Ser | Thr | Leu | Arg | |
| | 2150 | | | | 2155 | | | | | 2160 | | | | | |
| atg | gag | ttg | atg | ggc | tgt | gat | tta | aat | agt | tgc | agc | atg | cca | ttg | 6534 |
| Met | Glu | Leu | Met | Gly | Cys | Asp | Leu | Asn | Ser | Cys | Ser | Met | Pro | Leu | |
| | 2165 | | | | 2170 | | | | | 2175 | | | | | |
| gga | atg | gag | agt | aaa | gca | ata | tca | gat | gca | cag | att | act | gct | tca | 6579 |
| Gly | Met | Glu | Ser | Lys | Ala | Ile | Ser | Asp | Ala | Gln | Ile | Thr | Ala | Ser | |
| | 2180 | | | | 2185 | | | | | 2190 | | | | | |
| tcc | tac | ttt | acc | aat | atg | ttt | gcc | acc | tgg | tct | cct | tca | aaa | gct | 6624 |
| Ser | Tyr | Phe | Thr | Asn | Met | Phe | Ala | Thr | Trp | Ser | Pro | Ser | Lys | Ala | |

```
                     2195                2200                2205
cga ctt cac ctc caa ggg agg agt aat gcc tgg aga cct cag gtg           6669
Arg Leu His Leu Gln Gly Arg Ser Asn Ala Trp Arg Pro Gln Val
    2210                2215                2220 aat aat cca aaa gag tgg ctg caa gtg gac ttc cag aag aca atg           6714
Asn Asn Pro Lys Glu Trp Leu Gln Val Asp Phe Gln Lys Thr Met
    2225                2230                2235 aaa gtc aca gga gta act act cag gga gta aaa tct ctg ctt acc           6759
Lys Val Thr Gly Val Thr Thr Gln Gly Val Lys Ser Leu Leu Thr
    2240                2245                2250 agc atg tat gtg aag gag ttc ctc atc tcc agc agt caa gat ggc           6804
Ser Met Tyr Val Lys Glu Phe Leu Ile Ser Ser Ser Gln Asp Gly
    2255                2260                2265 cat cag tgg act ctc ttt ttt cag aat ggc aaa gta aag gtt ttc           6849
His Gln Trp Thr Leu Phe Phe Gln Asn Gly Lys Val Lys Val Phe
    2270                2275                2280 cag gga aat caa gac tcc ttc aca cct gtg gtg aac tct cta gac           6894
Gln Gly Asn Gln Asp Ser Phe Thr Pro Val Val Asn Ser Leu Asp
    2285                2290                2295 cca ccg tta ctg act cgc tac ctt cga att cac ccc cag agt tgg           6939
Pro Pro Leu Leu Thr Arg Tyr Leu Arg Ile His Pro Gln Ser Trp
    2300                2305                2310 gtg cac cag att gcc ctg agg atg gag gtt ctg ggc tgc gag gca           6984
Val His Gln Ile Ala Leu Arg Met Glu Val Leu Gly Cys Glu Ala
    2315                2320                2325 cag gac ctc tac                                                       6996
Gln Asp Leu Tyr
    2330

<210> SEQ ID NO 2
<211> LENGTH: 2332
<212> TYPE: PRT
<213> ORGANISM: homo sapiens

<400> SEQUENCE: 2

Ala Thr Arg Arg Tyr Tyr Leu Gly Ala Val Glu Leu Ser Trp Asp Tyr
 1               5                  10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175
```

-continued

Leu Val Cys Arg Glu Gly Ser Leu Ala Lys Glu Lys Thr Gln Thr Leu
             180                 185                 190

His Lys Phe Ile Leu Leu Phe Ala Val Phe Asp Glu Gly Lys Ser Trp
             195                 200                 205

His Ser Glu Thr Lys Asn Ser Leu Met Gln Asp Arg Asp Ala Ala Ser
             210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                 245                 250                 255

Val Ile Gly Met Gly Thr Thr Pro Glu Val His Ser Ile Phe Leu Glu
             260                 265                 270

Gly His Thr Phe Leu Val Arg Asn His Arg Gln Ala Ser Leu Glu Ile
             275                 280                 285

Ser Pro Ile Thr Phe Leu Thr Ala Gln Thr Leu Leu Met Asp Leu Gly
             290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Glu Pro Gln Leu Arg
                 325                 330                 335

Met Lys Asn Asn Glu Glu Ala Glu Asp Tyr Asp Asp Asp Leu Thr Asp
             340                 345                 350

Ser Glu Met Asp Val Val Arg Phe Asp Asp Asp Asn Ser Pro Ser Phe
             355                 360                 365

Ile Gln Ile Arg Ser Val Ala Lys Lys His Pro Lys Thr Trp Val His
             370                 375                 380

Tyr Ile Ala Ala Glu Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                 405                 410                 415

Gln Arg Ile Gly Arg Lys Tyr Lys Lys Val Arg Phe Met Ala Tyr Thr
             420                 425                 430

Asp Glu Thr Phe Lys Thr Arg Glu Ala Ile Gln His Glu Ser Gly Ile
             435                 440                 445

Leu Gly Pro Leu Leu Tyr Gly Glu Val Gly Asp Thr Leu Leu Ile Ile
             450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                 485                 490                 495

His Leu Lys Asp Phe Pro Ile Leu Pro Gly Glu Ile Phe Lys Tyr Lys
             500                 505                 510

Trp Thr Val Thr Val Glu Asp Gly Pro Thr Lys Ser Asp Pro Arg Cys
             515                 520                 525

Leu Thr Arg Tyr Tyr Ser Ser Phe Val Asn Met Glu Arg Asp Leu Ala
             530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
                 565                 570                 575

Ser Val Phe Asp Glu Asn Arg Ser Trp Tyr Leu Thr Glu Asn Ile Gln
             580                 585                 590

Arg Phe Leu Pro Asn Pro Ala Gly Val Gln Leu Glu Asp Pro Glu Phe

```
                595                 600                 605
Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
                645                 650                 655

Thr Phe Lys His Lys Met Val Tyr Glu Asp Thr Leu Thr Leu Phe Pro
                660                 665                 670

Phe Ser Gly Glu Thr Val Phe Met Ser Met Glu Asn Pro Gly Leu Trp
                675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
                725                 730                 735

Ile Glu Pro Arg Ser Phe Ser Gln Asn Ser Arg His Arg Ser Thr Arg
                740                 745                 750

Gln Lys Gln Phe Asn Ala Thr Thr Ile Pro Glu Asn Asp Ile Glu Lys
                755                 760                 765

Thr Asp Pro Trp Phe Ala His Arg Thr Pro Met Pro Lys Ile Gln Asn
770                 775                 780

Val Ser Ser Ser Asp Leu Leu Met Leu Leu Arg Gln Ser Pro Thr Pro
785                 790                 795                 800

His Gly Leu Ser Leu Ser Asp Leu Gln Glu Ala Lys Tyr Glu Thr Phe
                805                 810                 815

Ser Asp Asp Pro Ser Pro Gly Ala Ile Asp Ser Asn Asn Ser Leu Ser
                820                 825                 830

Glu Met Thr His Phe Arg Pro Gln Leu His His Ser Gly Asp Met Val
                835                 840                 845

Phe Thr Pro Glu Ser Gly Leu Gln Leu Arg Leu Asn Glu Lys Leu Gly
850                 855                 860

Thr Thr Ala Ala Thr Glu Leu Lys Lys Leu Asp Phe Lys Val Ser Ser
865                 870                 875                 880

Thr Ser Asn Asn Leu Ile Ser Thr Ile Pro Ser Asp Asn Leu Ala Ala
                885                 890                 895

Gly Thr Asp Asn Thr Ser Ser Leu Gly Pro Pro Ser Met Pro Val His
                900                 905                 910

Tyr Asp Ser Gln Leu Asp Thr Thr Leu Phe Gly Lys Lys Ser Ser Pro
                915                 920                 925

Leu Thr Glu Ser Gly Gly Pro Leu Ser Leu Ser Glu Asn Asn Asp
                930                 935                 940

Ser Lys Leu Leu Glu Ser Gly Leu Met Asn Ser Gln Glu Ser Ser Trp
945                 950                 955                 960

Gly Lys Asn Val Ser Ser Thr Glu Ser Gly Arg Leu Phe Lys Gly Lys
                965                 970                 975

Arg Ala His Gly Pro Ala Leu Leu Thr Lys Asp Asn Ala Leu Phe Lys
                980                 985                 990

Val Ser Ile Ser Leu Leu Lys Thr Asn Lys Thr Ser Asn Asn Ser Ala
                995                 1000                1005

Thr Asn Arg Lys Thr His Ile Asp Gly Pro Ser Leu Leu Ile Glu
                1010                1015                1020
```

```
Asn Ser Pro Ser Val Trp Gln Asn Ile Leu Glu Ser Asp Thr Glu
    1025            1030                1035

Phe Lys Lys Val Thr Pro Leu Ile His Asp Arg Met Leu Met Asp
    1040            1045                1050

Lys Asn Ala Thr Ala Leu Arg Leu Asn His Met Ser Asn Lys Thr
    1055            1060                1065

Thr Ser Ser Lys Asn Met Glu Met Val Gln Gln Lys Lys Glu Gly
    1070            1075                1080

Pro Ile Pro Pro Asp Ala Gln Asn Pro Asp Met Ser Phe Phe Lys
    1085            1090                1095

Met Leu Phe Leu Pro Glu Ser Ala Arg Trp Ile Gln Arg Thr His
    1100            1105                1110

Gly Lys Asn Ser Leu Asn Ser Gly Gln Gly Pro Ser Pro Lys Gln
    1115            1120                1125

Leu Val Ser Leu Gly Pro Glu Lys Ser Val Glu Gly Gln Asn Phe
    1130            1135                1140

Leu Ser Glu Lys Asn Lys Val Val Val Gly Lys Gly Glu Phe Thr
    1145            1150                1155

Lys Asp Val Gly Leu Lys Glu Met Val Phe Pro Ser Ser Arg Asn
    1160            1165                1170

Leu Phe Leu Thr Asn Leu Asp Asn Leu His Glu Asn Asn Thr His
    1175            1180                1185

Asn Gln Glu Lys Lys Ile Gln Glu Glu Ile Glu Lys Lys Glu Thr
    1190            1195                1200

Leu Ile Gln Glu Asn Val Val Leu Pro Gln Ile His Thr Val Thr
    1205            1210                1215

Gly Thr Lys Asn Phe Met Lys Asn Leu Phe Leu Leu Ser Thr Arg
    1220            1225                1230

Gln Asn Val Glu Gly Ser Tyr Asp Gly Ala Tyr Ala Pro Val Leu
    1235            1240                1245

Gln Asp Phe Arg Ser Leu Asn Asp Ser Thr Asn Arg Thr Lys Lys
    1250            1255                1260

His Thr Ala His Phe Ser Lys Lys Gly Glu Glu Glu Asn Leu Glu
    1265            1270                1275

Gly Leu Gly Asn Gln Thr Lys Gln Ile Val Glu Lys Tyr Ala Cys
    1280            1285                1290

Thr Thr Arg Ile Ser Pro Asn Thr Ser Gln Gln Asn Phe Val Thr
    1295            1300                1305

Gln Arg Ser Lys Arg Ala Leu Lys Gln Phe Arg Leu Pro Leu Glu
    1310            1315                1320

Glu Thr Glu Leu Glu Lys Arg Ile Ile Val Asp Asp Thr Ser Thr
    1325            1330                1335

Gln Trp Ser Lys Asn Met Lys His Leu Thr Pro Ser Thr Leu Thr
    1340            1345                1350

Gln Ile Asp Tyr Asn Glu Lys Glu Lys Gly Ala Ile Thr Gln Ser
    1355            1360                1365

Pro Leu Ser Asp Cys Leu Thr Arg Ser His Ser Ile Pro Gln Ala
    1370            1375                1380

Asn Arg Ser Pro Leu Pro Ile Ala Lys Val Ser Ser Phe Pro Ser
    1385            1390                1395

Ile Arg Pro Ile Tyr Leu Thr Arg Val Leu Phe Gln Asp Asn Ser
    1400            1405                1410
```

```
Ser His Leu Pro Ala Ala Ser Tyr Arg Lys Lys Asp Ser Gly Val
1415                1420                1425

Gln Glu Ser Ser His Phe Leu Gln Gly Ala Lys Lys Asn Asn Leu
1430                1435                1440

Ser Leu Ala Ile Leu Thr Leu Glu Met Thr Gly Asp Gln Arg Glu
1445                1450                1455

Val Gly Ser Leu Gly Thr Ser Ala Thr Asn Ser Val Thr Tyr Lys
1460                1465                1470

Lys Val Glu Asn Thr Val Leu Pro Lys Pro Asp Leu Pro Lys Thr
1475                1480                1485

Ser Gly Lys Val Glu Leu Leu Pro Lys Val His Ile Tyr Gln Lys
1490                1495                1500

Asp Leu Phe Pro Thr Glu Thr Ser Asn Gly Ser Pro Gly His Leu
1505                1510                1515

Asp Leu Val Glu Gly Ser Leu Leu Gln Gly Thr Glu Gly Ala Ile
1520                1525                1530

Lys Trp Asn Glu Ala Asn Arg Pro Gly Lys Val Pro Phe Leu Arg
1535                1540                1545

Val Ala Thr Glu Ser Ser Ala Lys Thr Pro Ser Lys Leu Leu Asp
1550                1555                1560

Pro Leu Ala Trp Asp Asn His Tyr Gly Thr Gln Ile Pro Lys Glu
1565                1570                1575

Glu Trp Lys Ser Gln Glu Lys Ser Pro Glu Lys Thr Ala Phe Lys
1580                1585                1590

Lys Lys Asp Thr Ile Leu Ser Leu Asn Ala Cys Glu Ser Asn His
1595                1600                1605

Ala Ile Ala Ala Ile Asn Glu Gly Gln Asn Lys Pro Glu Ile Glu
1610                1615                1620

Val Thr Trp Ala Lys Gln Gly Arg Thr Glu Arg Leu Cys Ser Gln
1625                1630                1635

Asn Pro Pro Val Leu Lys Arg His Gln Arg Glu Ile Thr Arg Thr
1640                1645                1650

Thr Leu Gln Ser Asp Gln Glu Glu Ile Asp Tyr Asp Asp Thr Ile
1655                1660                1665

Ser Val Glu Met Lys Lys Glu Asp Phe Asp Ile Tyr Asp Glu Asp
1670                1675                1680

Glu Asn Gln Ser Pro Arg Ser Phe Gln Lys Lys Thr Arg His Tyr
1685                1690                1695

Phe Ile Ala Ala Val Glu Arg Leu Trp Asp Tyr Gly Met Ser Ser
1700                1705                1710

Ser Pro His Val Leu Arg Asn Arg Ala Gln Ser Gly Ser Val Pro
1715                1720                1725

Gln Phe Lys Lys Val Val Phe Gln Glu Phe Thr Asp Gly Ser Phe
1730                1735                1740

Thr Gln Pro Leu Tyr Arg Gly Glu Leu Asn Glu His Leu Gly Leu
1745                1750                1755

Leu Gly Pro Tyr Ile Arg Ala Glu Val Glu Asp Asn Ile Met Val
1760                1765                1770

Thr Phe Arg Asn Gln Ala Ser Arg Pro Tyr Ser Phe Tyr Ser Ser
1775                1780                1785

Leu Ile Ser Tyr Glu Glu Asp Gln Arg Gln Gly Ala Glu Pro Arg
1790                1795                1800

Lys Asn Phe Val Lys Pro Asn Glu Thr Lys Thr Tyr Phe Trp Lys
```

```
            1805                1810                1815

Val Gln His His Met Ala Pro Thr Lys Asp Glu Phe Asp Cys Lys
    1820                1825                1830

Ala Trp Ala Tyr Phe Ser Asp Val Asp Leu Glu Lys Asp Val His
    1835                1840                1845

Ser Gly Leu Ile Gly Pro Leu Leu Val Cys His Thr Asn Thr Leu
    1850                1855                1860

Asn Pro Ala His Gly Arg Gln Val Thr Val Gln Glu Phe Ala Leu
    1865                1870                1875

Phe Phe Thr Ile Phe Asp Glu Thr Lys Ser Trp Tyr Phe Thr Glu
    1880                1885                1890

Asn Met Glu Arg Asn Cys Arg Ala Pro Cys Asn Ile Gln Met Glu
    1895                1900                1905

Asp Pro Thr Phe Lys Glu Asn Tyr Arg Phe His Ala Ile Asn Gly
    1910                1915                1920

Tyr Ile Met Asp Thr Leu Pro Gly Leu Val Met Ala Gln Asp Gln
    1925                1930                1935

Arg Ile Arg Trp Tyr Leu Leu Ser Met Gly Ser Asn Glu Asn Ile
    1940                1945                1950

His Ser Ile His Phe Ser Gly His Val Phe Thr Val Arg Lys Lys
    1955                1960                1965

Glu Glu Tyr Lys Met Ala Leu Tyr Asn Leu Tyr Pro Gly Val Phe
    1970                1975                1980

Glu Thr Val Glu Met Leu Pro Ser Lys Ala Gly Ile Trp Arg Val
    1985                1990                1995

Glu Cys Leu Ile Gly Glu His Leu His Ala Gly Met Ser Thr Leu
    2000                2005                2010

Phe Leu Val Tyr Ser Asn Lys Cys Gln Thr Pro Leu Gly Met Ala
    2015                2020                2025

Ser Gly His Ile Arg Asp Phe Gln Ile Thr Ala Ser Gly Gln Tyr
    2030                2035                2040

Gly Gln Trp Ala Pro Lys Leu Ala Arg Leu His Tyr Ser Gly Ser
    2045                2050                2055

Ile Asn Ala Trp Ser Thr Lys Glu Pro Phe Ser Trp Ile Lys Val
    2060                2065                2070

Asp Leu Leu Ala Pro Met Ile Ile His Gly Ile Lys Thr Gln Gly
    2075                2080                2085

Ala Arg Gln Lys Phe Ser Ser Leu Tyr Ile Ser Gln Phe Ile Ile
    2090                2095                2100

Met Tyr Ser Leu Asp Gly Lys Lys Trp Gln Thr Tyr Arg Gly Asn
    2105                2110                2115

Ser Thr Gly Thr Leu Met Val Phe Phe Gly Asn Val Asp Ser Ser
    2120                2125                2130

Gly Ile Lys His Asn Ile Phe Asn Pro Pro Ile Ile Ala Arg Tyr
    2135                2140                2145

Ile Arg Leu His Pro Thr His Tyr Ser Ile Arg Ser Thr Leu Arg
    2150                2155                2160

Met Glu Leu Met Gly Cys Asp Leu Asn Ser Cys Ser Met Pro Leu
    2165                2170                2175

Gly Met Glu Ser Lys Ala Ile Ser Asp Ala Gln Ile Thr Ala Ser
    2180                2185                2190

Ser Tyr Phe Thr Asn Met Phe Ala Thr Trp Ser Pro Ser Lys Ala
    2195                2200                2205
```

```
Arg Leu His Leu Gln Gly Arg Ser Asn Ala Trp Arg Pro Gln Val
    2210            2215                2220
Asn Asn Pro Lys Glu Trp Leu Gln Val Asp Phe Gln Lys Thr Met
    2225            2230                2235
Lys Val Thr Gly Val Thr Thr Gln Gly Val Lys Ser Leu Leu Thr
    2240            2245                2250
Ser Met Tyr Val Lys Glu Phe Leu Ile Ser Ser Ser Gln Asp Gly
    2255            2260                2265
His Gln Trp Thr Leu Phe Phe Gln Asn Gly Lys Val Lys Val Phe
    2270            2275                2280
Gln Gly Asn Gln Asp Ser Phe Thr Pro Val Val Asn Ser Leu Asp
    2285            2290                2295
Pro Pro Leu Leu Thr Arg Tyr Leu Arg Ile His Pro Gln Ser Trp
    2300            2305                2310
Val His Gln Ile Ala Leu Arg Met Glu Val Leu Gly Cys Glu Ala
    2315            2320                2325
Gln Asp Leu Tyr
    2330
```